(12) United States Patent
Murakami

(10) Patent No.: US 8,317,168 B2
(45) Date of Patent: Nov. 27, 2012

(54) MIXER, MIXING DEVICE AND UNIT FOR MEASURING MEDICAL COMPONENT

(75) Inventor: Motoaki Murakami, Shizuoka (JP)

(73) Assignee: Nikkiso Co., Ltd., Tokyo (JP)

( * ) Notice: Subject to any disclaimer, the term of this patent is extended or adjusted under 35 U.S.C. 154(b) by 896 days.

(21) Appl. No.: 12/295,721

(22) PCT Filed: Apr. 4, 2007

(86) PCT No.: PCT/JP2007/000367
§ 371 (c)(1),
(2), (4) Date: Apr. 8, 2009

(87) PCT Pub. No.: WO2007/125642
PCT Pub. Date: Nov. 8, 2007

(65) Prior Publication Data
US 2009/0218704 A1  Sep. 3, 2009

(30) Foreign Application Priority Data
Apr. 5, 2006  (JP) ................................ 2006-104741

(51) Int. Cl.
*B01F 3/04* (2006.01)
(52) U.S. Cl. .............................. 261/109; 96/215; 96/356
(58) Field of Classification Search ................. 261/108, 261/109, 119.1, 123; 96/215, 356, 358
See application file for complete search history.

(56) References Cited

U.S. PATENT DOCUMENTS

| | | | | |
|---|---|---|---|---|
| 453,806 A | * | 6/1891 | Grutzner et al. | 261/160 |
| 1,661,980 A | * | 3/1928 | Voigt | 181/260 |
| 1,813,959 A | * | 7/1931 | Romanoff | 261/119.1 |
| 1,936,305 A | * | 11/1933 | Leffler | 261/123 |
| 2,824,728 A | * | 2/1958 | Crawford | 261/119.1 |
| 3,962,381 A | * | 6/1976 | Farrish et al. | 261/141 |
| 4,005,014 A | * | 1/1977 | Wikey | 210/192 |
| 4,181,614 A | * | 1/1980 | Steenhorst | 210/221.2 |
| 4,276,059 A | * | 6/1981 | Macierewicz | 95/262 |
| 5,034,029 A | * | 7/1991 | Brattan et al. | 95/149 |
| 5,054,422 A | * | 10/1991 | Nojima et al. | 119/215 |
| 5,651,939 A | * | 7/1997 | Murrer et al. | 422/28 |
| 6,270,063 B1 | * | 8/2001 | Carrillo | 261/122.1 |

FOREIGN PATENT DOCUMENTS

| | | |
|---|---|---|
| JP | 8114538 | 5/1996 |
| JP | 2001165939 | 6/2001 |
| JP | 2003302399 | 10/2003 |
| JP | 2004093558 | 3/2004 |
| JP | 2005-030906 | 2/2005 |
| JP | 2006112881 | 4/2006 |

* cited by examiner

*Primary Examiner* — Charles Bushey
(74) *Attorney, Agent, or Firm* — McDermott Will & Emery LLP

(57) ABSTRACT

This invention provides a mixer without a rotational or similar structure, capable of mixing quickly several liquids including at least one liquid being prone to gel or solidify, a mixing device with the mixer incorporated, and a medical component-measuring unit capable of reducing the formation of thrombi and accurately measuring the concentration of glucose, and with a small time constant, which unit can be incorporated into medical support devices, such as artificial endocrine pancreas devices. The mixer has an air bubble-trapping structure for temporarily trapping air bubbles supplied to a surface of a mixing channel through which liquids to be mixed flow. The mixing device has the mixer, an air bubble supplier or generator to make air bubbles exist in the mixing channel, and a liquid supplier for supplying liquids to be mixed to a liquid inlet. The medical component-measuring unit has the mixer or the mixing device.

13 Claims, 19 Drawing Sheets

MIXER, MIXING DEVICE AND UNIT FOR MEASURING MEDICAL COMPONENT

CROSS REFERENCE TO PRIOR RELATED APPLICATIONS

This is a U.S. national phase application under 35 U.S.C. §371 of International Patent Application No. PCT/JP2007/000367 filed Apr. 4, 2007, and claims the benefit of Japanese Patent Application No. 2006-104741 filed Apr. 5, 2006. The International Application was published in Japanese on Nov. 8, 2007 as WO 2007/125642 A1 under PCT Article 21 (2). The contents of these priority applications are incorporated, in their entireties, into the present disclosure by reference.

BACKGROUND OF THE INVENTION

1. Field of the Invention

The present invention relates to a mixer, a mixing device, and a medical component-measuring unit. More particularly, the present invention relates to a mixer capable of mixing quickly several liquids including at least one liquid that is prone to easily gel or solidify, which mixer has a structure preventing the liquid from gelling. The invention also relates to a mixing device, with the mixer incorporated, capable of mixing the several liquids so as not to cause the liquid to gel or solidify. The present invention further relates to a medical component-measuring unit including the mixer or the mixing device.

2. Description of the Related Art

When several liquids including at least one liquid that is prone to gel or solidify are mixed, the mixing operation must be done quickly and adopt a measure to prevent the liquid from gelling or solidifying. In, for example, an artificial endocrine pancreas device, the concentration of the glucose component in blood is measured by measuring a mixed liquid of a blood sample taken from a patient and a reagent. In order to accurately measure the glucose concentration, it is necessary to mix the blood sample and the reagent uniformly and a measurement has to be done in such a quick manner that the measurement is completed before the blood sample coagulates in the fluid channels. Please note that the word "coagulate" includes the meanings of "gel" and "solidify".

As a technique of mixing several liquids flowing in micro-scale channels are proposed "microchannels for helical flow" (Non-patent Document 1). The following is a passage from non-patent document 1: "There is a micro-mixer which causes a helical flow in a microchannel by oblique grooves inscribed in the bottom of the channel, which increases contact interfaces of samples and expedites diffusion and mixing. (A. D. Stroock, et al., Chaotic Mixer for Microchannels, Science, Vol. 295, pp. 647-651, 2002) We thought that smaller pitches of the helix of a helical flow would improve the efficiency of mixing and proposed a "microchannel for high-efficiency helical flow" in which oblique grooves are formed in the three walls of the channel, as shown in FIG. 7 (b)." The proposed "microchannel for high-efficiency helical flow" is considered to be a very excellent device when it is applied to a micro-scale channel that has a relatively long channel compared to the area of the transverse section of the channel. However, some more improvement is necessary for applications, such as artificial endocrine pancreas devices, which should have a channel as short as possible to reduce a time period for which the mixed liquid flows through the channel, or the time constant.

We conducted a search was conducted on B01F5/00@D as FI code with patent documents that were published on and after Jun. 1, 1989. Some of the documents are listed below.
Patent Document 1: JP 2006-015292 A
Patent Document 2: JP 2006-015272 A
Patent Document 3: JP 2006-007063 A
Patent Document 4: JP 2005-342944 A
Patent Document 5: JP 2005-324080 A
Patent Document 6: JP 2005-319419 A
Patent Document 7: JP 2005-314424 A
Patent Document 8: JP 2005-313042 A
Patent Document 9: JP 2005-305219 A
Patent Document 10: JP 2005-288254 A
Patent Document 11: JP 2005-279542 A
Patent Document 12: JP 2005-246184 A
Patent Document 13: JP 2005-238232 A
Patent Document 14: JP 2005-230586 A
Patent Document 15: JP 2005-224799 A
Non-patent Document 1: http://www.shoji.com-m.waseda.ac.jp/~mf/,fjp/rasen.htm When several liquids, each in a very small amount, which have a small flow velocity and forms laminar flow, are mixed, interlayer mixing or mixing between the layers does not progress. Besides, it is difficult to place a rotatable mixer in a channel with a small diameter to mix several kinds of liquids each in small amounts while they are being transferred. Even if such a mixer is placed in the channel, it makes the structure of the device complicated. When a blood sample and a reagent are mixed with a mixing device or by other structures, the device and structures become obstacles against the fluid flow, and the liquids are caught by the obstacles and remain on places thereof, which leads to the formation of thrombi. Also, coiled tubes, made by winding a tube like a coil, are employed as a device mixing a blood sample with a reagent in applications such as artificial endocrine pancreas devices. The coiled tube is so designed that the mixing of a blood sample and a reagent is achieved while the blood sample and the reagent are passing through the coiled tube gradually. Although this kind of coiled tubes somehow achieves the mixing of a blood sample and a reagent, the length of the coiled tube reaches as much as 320 mm. Artificial endocrine pancreas devices, employing such a long coiled tube as mixing device, have a large time constant, which is problematic with this kind of devices.

SUMMARY OF THE INVENTION

An objective of the present invention is to provide a mixer without rotating structures such as mixing blades, capable of mixing quickly several liquids including at least one liquid that is prone to gel or solidify easily. It is also the objective to provide a mixing device capable of quickly mixing several liquids including at least one liquid that is prone to gel or solidify by utilizing air bubbles, which mixing device has a structure by which the liquids are mixed uniformly without causing the liquid to gel or solidify. A still further objective is to provide a medical component-measuring unit capable of reducing the formation of thrombi and accurately measuring the concentration of glucose, and with a small time constant, made by incorporation of the mixer or the mixing device, which unit, in turn, can be incorporated into medical support devices, such as artificial endocrine pancreas devices.

These objectives can be solved by a mixer having an air bubble-trapping structure for temporarily trapping air bubbles supplied to a surface of a mixing channel through which liquids to be mixed flow.

The mixer may include a liquid inlet at a part upstream of the mixing channel from which the liquids are supplied, and a liquid outlet at a part downstream thereof from which the liquids are discharged.

The mixer may also include a mixing channel that is inclined at an angle of 20 to 90 degrees to a horizontal line.

The mixer may also include an air bubble-trapping structure placed in a ceiling of the mixing channel.

The mixer may also include an air bubble-trapping structure that is at least one selected from grooves, recesses and projections formed in the ceiling.

The mixer may also include an air bubble-trapping structure that is hydrophobic parts formed on an inner surface of the mixing channel through which the liquids flow.

The mixer may also include a liquid inlet that is located at a higher level than the liquid outlet.

The mixer may also include an air bubble supplier or an air bubble generator positioned in the mixing channel included in the mixer to make air bubbles exist in the mixing channel; and a liquid supplier for supplying liquids to be mixed one by one or simultaneously to the liquid inlet described in the second means to feed the liquids into the mixing channel.

The mixer may also include a medical component-measuring unit.

In the mixer according to the present invention, liquids to be mixed as well as air bubbles are supplied into the mixing channel. Air Bubbles that have been supplied are temporarily trapped by the air bubble-trapping structure. The trapping is done so that air bubbles are aligned in a row or continuously. Alternatively air bubbles may be trapped so that they are scattered at random intervals between them without contacting each other. Trapped air bubbles aligned continuously and/or scattered randomly make liquids supplied to this mixer thread their way through the air bubbles. Moreover, the path of the liquids is changed when the air bubbles change their trapping sites. This change in the path makes the liquids mix with each other and expedites the mixing. Therefore the function of the air bubble-trapping structure of the mixer according to the present invention, which temporarily traps air bubbles, is unique. Also, air bubbles that were once trapped and are released from the trapping structure move randomly in the liquids, which also expedites mixing of the liquids. The liquids are supplied to the mixing channel of the mixer from the liquid inlet that is placed at a location upstream of the mixing channel. The liquids that have been mixed during their passing through the mixing channel are discharged from the liquid outlet. The liquids discharged from this liquid outlet sometimes include air bubbles. When the mixing channel is provided with a gas-liquid separator, the mixed liquids from which air bubbles have been removed are discharged.

Although the mixer according to the present invention may be placed horizontally, it can also be positioned aslant, which is preferable. In the latter case, the angle at which the mixer is inclined should be from 20 degrees to 90 degrees to the horizontal face. When the mixer is inclined in this way, it should preferably be so positioned that the liquid inlet is at an upper side, liquid outlet at a lower side, and the air bubble-trapping structure is in or on the ceiling of the mixing channel. When the mixer is in such a position, the liquids supplied from the liquid inlet, which is located at an upper side, fall gravitationally or by the force of discharging the liquids exerted by a suck-and-discharge device such as a pump. Air bubbles that have been introduced into the mixer and exist in the mixing channel are temporarily trapped by the air bubble-trapping structure. The trapped air bubbles are released from the trapping structure after a predetermined period of time and let to be outside the trapping structure temporarily. Some of the released air bubbles tend to rise toward the surface against the downward flow of the liquids supplied from the liquid inlet, which is located at the upper place, while the others move downward with the downward flow of the liquids. The air bubbles moving upward and those moving downward are caught by the trapping structure and kept in it for a short time again. Then, the trapped air bubbles are released from the trap structure again, and some of the re-released air bubbles tend to rise toward the surface against the downward flow of the liquids supplied from the liquid inlet, which is located at the upper place, while the others move downward with the downward flow of the liquids, in the same way. The air bubbles are finally discharged from the liquid outlet with the downward flow. Irregular movements of the air bubbles and local disturbances of the fluid flow caused by complicated movements of the air bubbles that repeat upward and downward movements, or the movement of rising toward the surface against the liquid flow and that of descending with it, further expedite mixing of the liquids. Moreover, when the liquids include blood, the formation of thrombi can be prevented because thrombus-causing substances that may possibly be produced in the mixing channel adhere to the air bubbles and are discharged from the liquid outlet with them.

The air bubble-trapping structure may have various shapes, such as grooves, recesses, or projections. In addition to, or in place of these shapes, the air bubble-trapping structure may be hydrophobic parts formed on a surface of the mixing channel. In this invention, air bubbles are trapped in the grooves and/or recesses, and the air bubbles are aligned continuously or scattered in them. As a result, the grooves and recesses cannot be places in which liquids prone to gel or solidify remain; on the contrary, the grooves and recesses form a dynamic mixing area where liquids are mixed with each other helped by the movements of air bubbles. Even if coagula made by gelling or solidification are formed on the surfaces of the air bubbles, large coagula that may be a factor in causing trouble cannot be easily formed because the air bubbles per se are discharged.

In conclusion, the present invention provides a mixer which is capable of mixing liquids each in very small amounts quickly and uniformly, and has a structure capable of preventing a liquid that is prone to gel or solidify from gelling or solidifying when it is mixed with other liquids, actually a very simple structure in order to prevent the gelation and solidification during its use.

Various means may be employed to introduce or make air bubbles, which show the mixing function, exist in the mixer. Examples of the means for making air bubbles exist in the mixer are an air bubble supplier and an air bubble generator. The air bubble supplier is a device for supplying air bubbles into the mixing channel, while the air bubble generator is a device for generating air bubbles. The air bubble generator may be used alone as a device to generate air bubbles in the liquids in the mixer, or may be used in combination with the air bubble supplier as a device to generate air bubbles to be supplied to the liquid inlet.

The mixer according to the present invention may advantageously be used to mix several kinds of liquids that are sent in the state of a laminar flow at a flow velocity of not more than 100 mL/hour. Generally, it is considered to be difficult to uniformly mix liquids in the state of a laminar flow that flow at a velocity of, for example, not more than 100 mL/hour in a coiled tube. Even if liquids in the state of a laminar flow are fed to the mixer of the invention as they are, the mixer will uniformly mix the liquids with each other in the mixing channel thereof by the random movements of air bubbles.

The mixing device having the air bubble supplier or air bubble generator as described above, the mixer, and a liquid supplier for supplying several kinds of liquids to the mixer is capable of mixing quickly and uniformly several kinds of liquids including at least one liquid that is prone to gel or solidify, by the aid of air bubbles, without employing such structures as mechanical mixers or stirrers.

The medical component-measuring unit, with the mixer or the mixing device incorporated, is capable of accurately measuring the concentration of glucose having a small time constant, once it is attached to a medical support device such as an artificial endocrine pancreas device.

DESCRIPTION OF THE PREFERRED EMBODIMENTS

Figure 1:
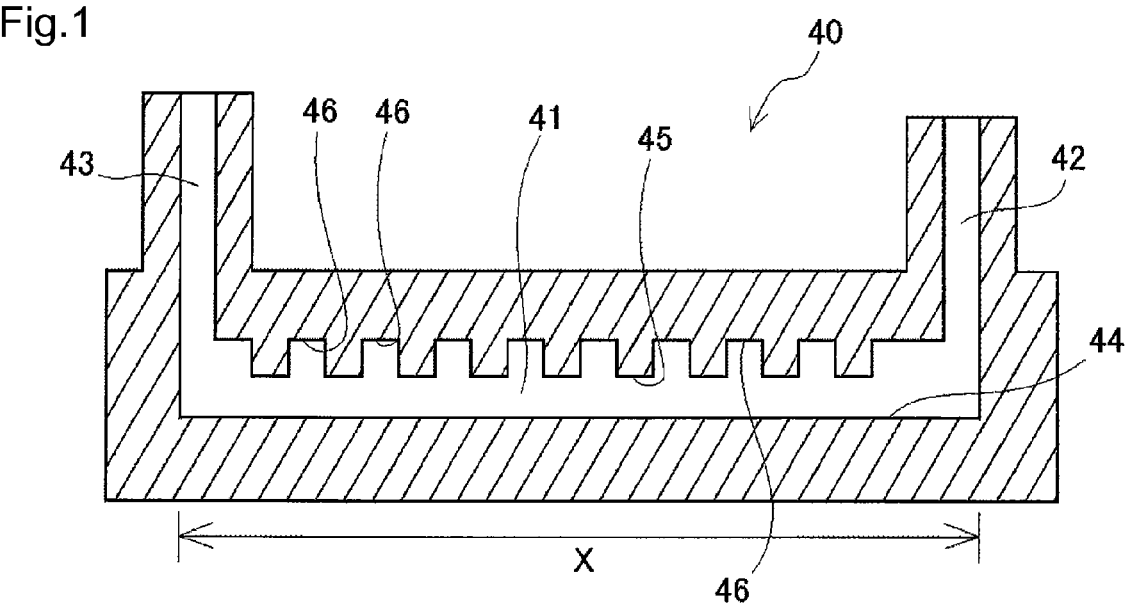
FIG. 1 is a longitudinal section showing a mixer, which is an example of the present invention.

As shown in FIG. 1, the mixer 40 has a mixing channel 41, a liquid inlet 42 and a liquid outlet 43. The mixing channel 41 is in the shape of a chamber with a bottom 44 and a ceiling 45. The ceiling 45 has a plan view in the shape of a general rectangle with a longer side parallel to the liquid flow and a shorter side perpendicular to the liquid flow. The ceiling 45 is provided with the liquid inlet 42 at one end thereof, and the liquid outlet 43 at the other end thereof. When the mixing channel 41 is designed so that liquids in a very small amount flow through it, the mixing channel typically has such dimensions that the distance between the bottom 44 and the ceiling 45 is from 0.1 to 2 mm, the length along the axis of the channel between the liquid inlet 42 and the liquid outlet 43 is from 5 to 50 mm, the inner diameter of the opening of the liquid inlet 42 is from 0.1 to 3 mm, and the inner diameter of the opening of the liquid outlet 43 is from 0.1 to 3 mm. The mixer of the present invention is capable of mixing liquids with each other irrespective of their flow rate, and is particularly suitable for mixing liquids in the state of a laminar flow sent into the mixer through the liquid inlet 42 at a flow rate of not more than 100 mL/hour.

The mixer may also be utilized for operations other than mixing several kinds of liquids each in very small amounts. The dimensions of the mixing channel may be designed appropriately, depending on the volume of the liquids to be mixed.

Figure 2:
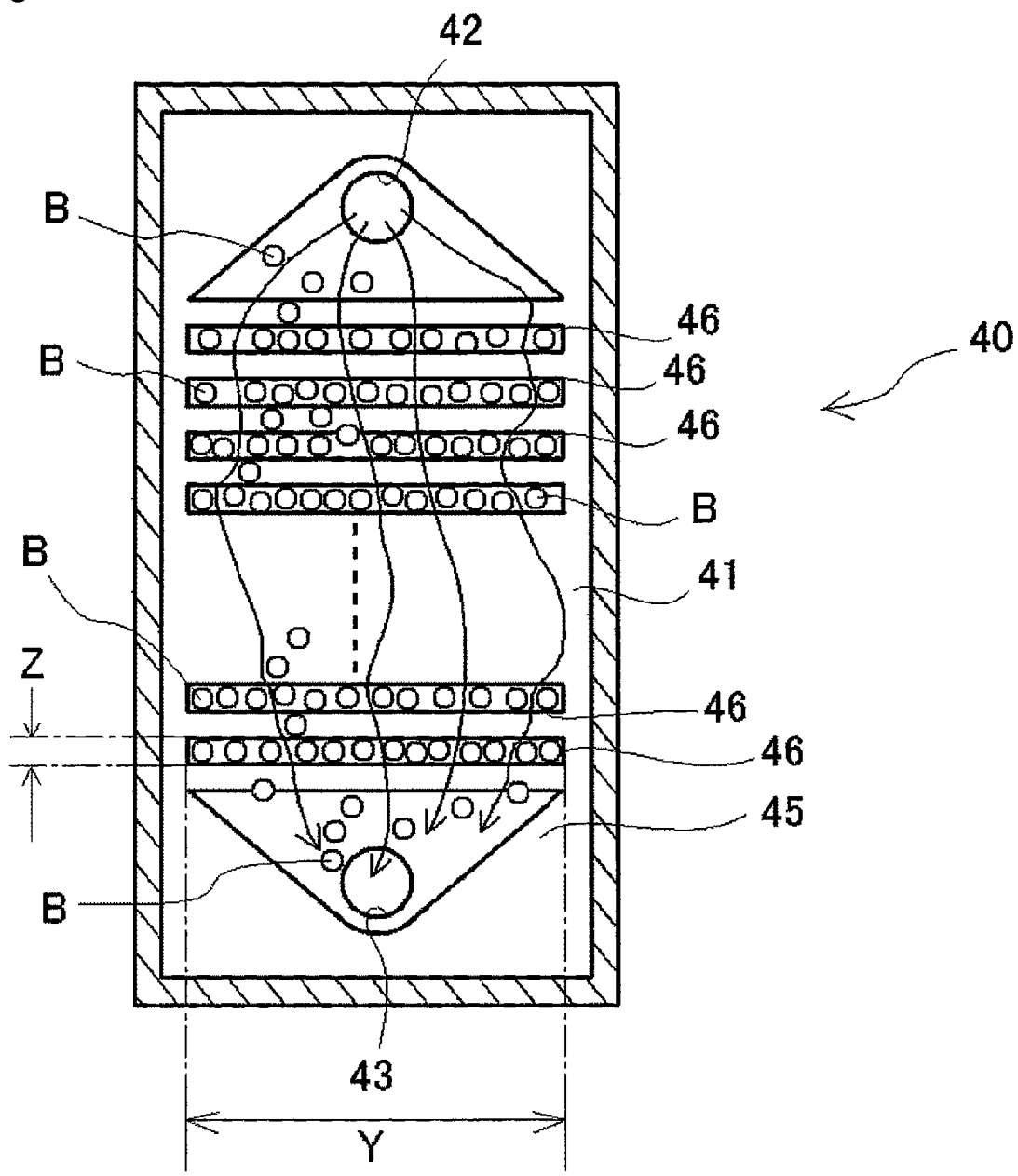
FIG. 2 is a horizontal section showing a mixer, which is an example of the present invention.

Grooves 46 as an example of the bubble trapping structure are formed in the ceiling 45 of the mixing channel 41. The grooves, which are parallel with each other, are formed in the ceiling 45 perpendicularly to the axis running from the liquid inlet 42 to the liquid outlet 43, or arrow X with barbs at both ends shown in FIG. 1. The grooves 46 have the same shape. In this example, as shown in FIGS. 1 and 2, each groove 46 is so formed that the transverse cross section thereof is in the shape of a rectangle. As shown in FIG. 2, each groove 46 typically has a length Y of 0.5 to 10 mm, a width Z of 0.1 to 3 mm, and a depth H of 0.1 to 3 mm (See FIG. 3). Air bubbles in the mixer 40 have a typical bubble size of 0.3 to 3 mm, and these tiny air bubbles B are caught, continuously or at intervals, in the grooves 46 with the described dimensions formed in the ceiling. Many air bubbles B that have been trapped for a short time in the grooves 46 are moved within the grooves 46 by the force of the liquid flow, whereby the liquids in the grooves 46 are expelled from the grooves to the outside, which leads to an inflow of a new portion of the liquids into the grooves 46. Also, the trapped air bubbles are released from the grooves 46 by the force of the liquids flowing in the mixing channel. As a whole, air bubbles B randomly move in the mixing channel.

These random movements of the air bubbles expedite the mixing of the several kinds of liquids flowing in the mixing channel. Also, while air bubbles are being temporarily trapped in the air bubble-trapping structure, the liquids thread their way through the trapped air bubbles. Moreover, the liquids change flow paths every time the air bubbles change their trapping sites. The threading and the changes in the threading flow paths also serve to expedite the mixing. Observation of the movements of the liquids and air bubbles revealed that the width of a groove and the bubble size of an air bubble should meet a certain requirement to perform efficient mixing. Specifically, the width of a groove should be from 20 to 80% of the bubble size of an air bubble. When the ratio of the width to the bubble size is within this range, air bubbles in the mixing channel easily enter the grooves and are trapped, and air bubbles trapped in the grooves are easily released from the grooves. The quickness and easiness of the trapped-and-released movements of air bubbles expedite another kind of movements, or such movements of the liquids that the liquids flow into the grooves and are discharged from them. Air bubbles mix the liquids not only by their simple existence and non-existence in the grooves, but also by their changes in sites in the grooves. Air bubbles that have been released from the grooves and set free in the mixing channel move upward against the force of gravity, and are also conveyed toward the liquid outlet by the liquids flowing in the mixing channel. As a result, air bubbles do complicated movements, which expedites the mixing of the several kinds of liquids in the mixing channel.

The number of the grooves formed in the ceiling between the liquid inlet 42 and the liquid outlet 43 are normally from 3 to 12. When the number of the grooves is less than 3, the mixing effects of air bubbles cannot be expected. On the other hand, if the number of the grooves is more than 12, the length of the mixing channel between the liquid inlet and the liquid outlet becomes large, which may increase the time constant of the medical component-measuring unit with this mixer to a considerable extent when it is attached to an artificial endocrine pancreas device and used to measure the concentration of glucose.

Figure 3:
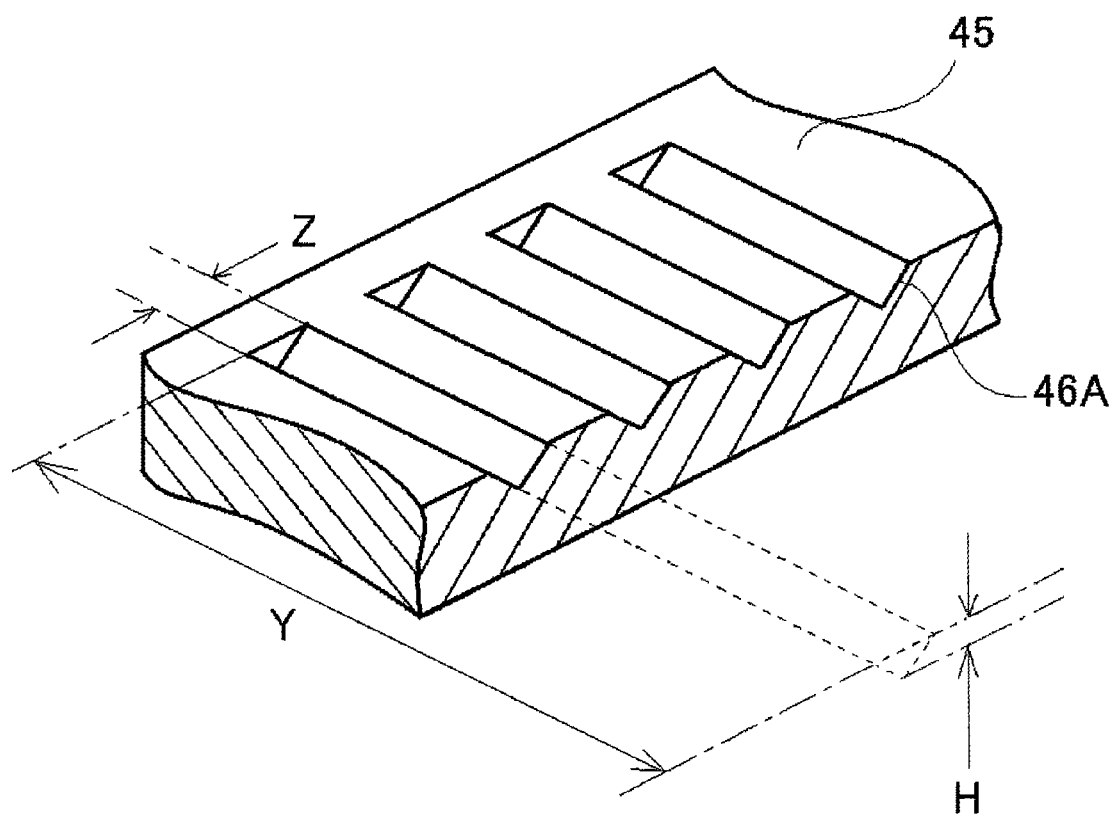
FIG. 3 is a partially cutaway perspective view showing another example of the air bubble-trapping structure in a mixer according to the present invention.

The air bubble trapping structure of the present invention are not limited to grooves having a square-shaped or rectangle-shaped transverse cross section as shown in FIGS. 1 and 2. Another example of the air bubble trapping structure is a grooves 46A shown in FIG. 3. These grooves 46A are formed in the ceiling 45, arranged parallel with each other. Each groove 46A is perpendicular to the axis running from the liquid inlet 42 to the liquid outlet 43, or arrow X with barbs at both ends shown in FIG. 1. The grooves 46A have the same shape. In this example, as shown in FIG. 3, each groove 46A is so formed that the transverse cross section thereof is in the shape of an inverted triangle. The transverse cross sections of the respective grooves 46A may be the same, similar figures, or different from each other. As shown in FIG. 3, each groove 46A typically has a length Y of 0.5 to 10 mm, a width Z of 0.1 to 3 mm, and a largest depth H of 0.1 to 3 mm. Air bubbles in the mixer 40 with the typical bubble size described hereinbefore are caught in the grooves 46A with the described dimensions, move within the grooves 46A by the force of the liquids flowing in the mixing channel, and released from the grooves 46A. As a whole, air bubbles randomly move in the mixing channel, which provides the same effects as the embodiment where in the grooves 46A with a rectangle-shaped transverse cross section are employed as the air bubble trapping structure. The transverse cross section of each groove may be in the shape of a semicircle or a half ellipse. Also, the number of the grooves formed in the ceiling 45 of the mixing channel 41 is not limited. Moreover, the grooves do not have to run perpendicular to the axis going from the liquid inlet 42 to the liquid outlet 43, but may be oriented at a predetermined angle to the axis. Furthermore, the grooves do not have to be formed separately from each other, as shown in FIGS. 1 and 2, but they may communicate with each other. Specifically, the grooves may form a pattern, for example, in the shape of a lattice, such as a tetragonal lattice, a triangular lattice, or a hexagonal lattice, in the ceiling. The pattern, made by the grooves arranged and formed in the ceiling, may also include repeating fylfots; a miedasuki, a Japanese traditional pattern made by diamonds repeating with their sides shared by adjoining diamonds, each side of which is made by three parallel lines, or grooves in this invention; an ajiro, another Japanese traditional pattern similar to herringbone; a pattern of concentric circles; or any other repeating patterns.

Figure 4:
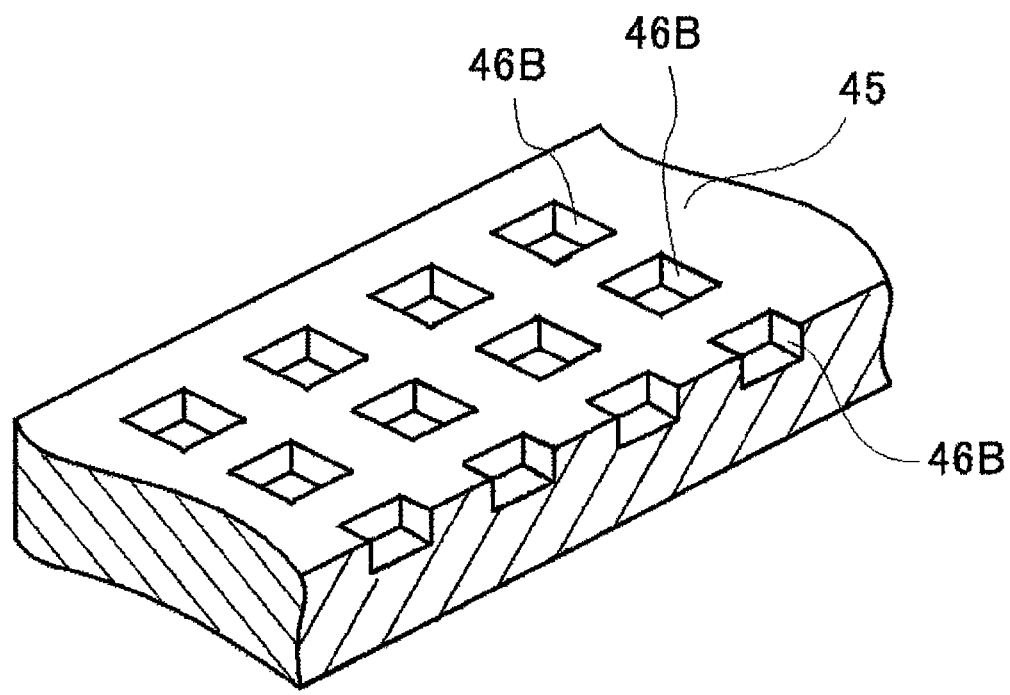
FIG. 4 is a partially cutaway perspective view showing still another example of the air bubble-trapping structure in a mixer according to the present invention.

Also, the air bubble trapping structure may be made by recesses 46B shown in FIG. 4. As shown in the figure, the opening of each recess 46B in the ceiling 45 is in the shape of a tetragon, and the bottom of the recess 46B is also in the shape of a tetragon. Many recesses 46B are laid out in the ceiling 45 so that non-recessed parts form a grid. The shape of the opening of each recess may be another shape as well, such as a circle, an ellipse, or a triangle.

Figure 5:
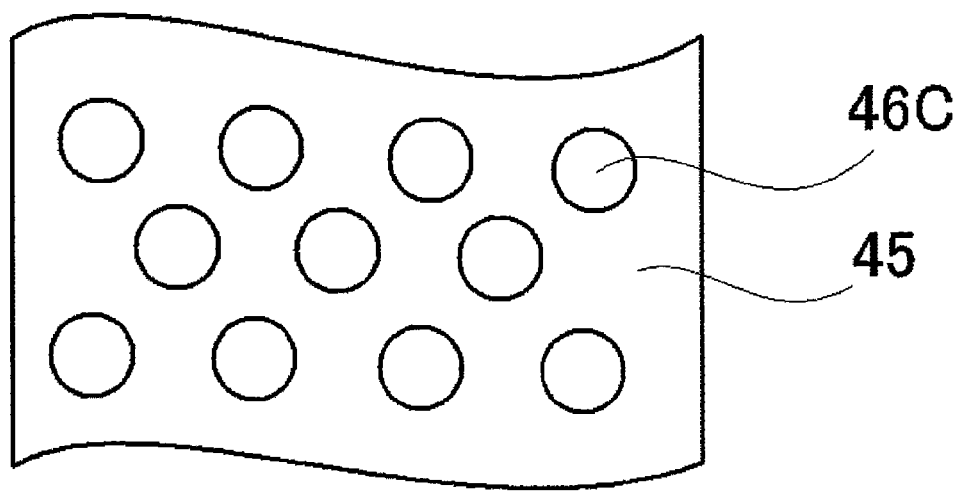
FIG. 5 is a partially cutaway perspective view showing a further example of the air bubble-trapping structure in a mixer according to the present invention.

The air bubble trapping structure does not have to be grooves or recesses, but may be projections 46C protruding from the surface of the ceiling 45, as shown in FIG. 5. The free end of each projection 46C may have any shape, examples of which include a circle, an ellipse, a triangle and a tetragon. The number of the projections 46C may be decided appropriately depending on the dimensions of the mixing channel and/or other factors. The distance between adjacent projections is adjusted depending on the average particle size of the air bubbles in the mixing channel. Normally, the distance should preferably be from 20 to 80% of the average particle size of the air bubbles.

The air bubble trapping structure may be things other than mechanical structures such as the grooves, the recesses and the projections, as long as it is capable of making air bubbles in the mixing channel stay at parts on the ceiling for a short time, releasing them from the parts to let them be outside the trapping structure temporarily, and letting them move randomly in the liquids flowing in the channel. Specifically, the trapping structure may be hydrophobic parts made on a smooth surface of the ceiling.

The hydrophobic parts may be realized in various ways, as long as the parts have the function of adsorbing air bubbles in the mixing channel. One example is a coating of a high polymer with hydrophobic groups, formed on the ceiling. Examples of the high polymer with hydrophobic groups may include high polymers having fluorine atoms, such as polytetrafluoro-ethylene, which is often abbreviated to PTFE; a copolymer of ethylene tetrafluoride and a perfluoroalkoxyethylene, which is often abbreviated to PFA; and a perfluoroethylene-propene copolymer, which is often abbreviated to FEP.

The coating may cover all or parts of the smooth surface of the ceiling without geometric structures such as the grooves, the recesses and the projections. Furthermore, the coating may cover the surfaces of the grooves, recesses, or projections formed in or on the ceiling as well. In the latter case, the air bubble-trapping structure is made by at least one of the grooves, the recesses and the projections formed in or on the ceiling, and the coating of a high polymer with hydrophobic groups that covers them. The air bubble-trapping structure made by the combination of the coating and at least one of the grooves, the recesses and the projections show more excellent mixing performance than the trapping structure made only by the grooves, the recesses and/or the projections.

The hydrophobic parts may be formed not only by the high polymer but also by inorganic substances with hydrophobicity. Examples of such inorganic substances may include zirconia, yttria, titania, etc. made by appropriate known methods such as a sol-gel process or a sputtering method.

Methods for applying a high polymer or an inorganic substance that provides the coated surface with hydrophobicity, to the ceiling may include, for example, a method comprised of coating the ceiling with a solution or a dispersion including the high polymer or the inorganic substance, or spraying the solution or the dispersion to the ceiling. Methods of providing all or parts of the smooth ceiling, or the ceiling having the grooves, the recesses or the projections with the hydrophobic parts are not limited to the mentioned method, but may include various methods. For example, one of the methods is providing the ceiling with a coating made of a hydrophobic group-introduced resin prepared by modifying parts of a hydrophobic group-containing resin by introducing further hydrophobic groups into it, or another kind of hydrophobic group-introduced resin prepared by modifying parts of a hydrophobic group-containing resin by introducing hydrophobic groups into it; or a laminate film prepared by applying a layer of a hydrophobic resin onto parts of the surface of a hydrophilic resin film, or another kind of laminate film prepared by applying a layer of a hydrophilic resin onto parts of the surface of a hydrophobic resin film.

The ceiling with hydrophobic parts may be made by attaching a member with hydrophobic parts to the surface of the ceiling base that does not have hydrophobicity. Also, the ceiling may be made by the two-color molding method so that all or parts of the surface of the ceiling have hydrophobic parts. Various methods other than the above-mentioned may be employed to provide the ceiling with hydrophobic parts. One further example is to form hydrophobic films on the surface of a hydrophilic ceiling by vapor deposition or sputtering. Employment of the photo-etching technique will make it possible to selectively form the hydrophobic parts with any shape. The photo-etching technique for silicone wafers may also be utilized to provide the ceiling with hydrophobic parts. An example of this method may include the step of making a ceiling out of monocrystal silicon, the step of oxidizing the monocrystal silicon by heating to partly change it to silicon oxide, and the step of subjecting the obtained to photo-etching. Thus, the ceiling has parts made of silicon oxide, or glass, which have a large hydrophilicity, and parts made of monocrystal silicon, which have little hydrophilicity. This method is capable of imparting flexibility to the design of the ceiling because the area, number and shape of the hydrophobic parts formed on the ceiling can be controlled at the designer's discretion. Generally, the method of forming the hydrophobic parts, and the number, area and shape of the hydrophobic parts are not specially limited and various methods and techniques may be employed to form them; the hydrophobic parts of the present invention serve to expedite mixing liquids by adsorbing and releasing air bubbles, and making the air bubbles move dynamically in the liquids.

The mixer with this air bubble-trapping structure may be placed so that the ceiling lies horizontally. However, in order to expedite the mixing more effectively, the mixer should be so placed that the axis running from the liquid inlet to the liquid outlet is inclined at an angle from 20 degrees to 90 degrees, preferably from 60 degrees to 90 degrees to the horizontal line, with the liquid inlet at the upper side and the liquid outlet at the lower side. When the mixer stands upright or slants in this say, the downward flow of the liquids introduced into the mixing channel from the liquid inlet located at the upper side, coupled with the upward movement of air bubbles in the mixing channel, stirs the several kinds of liquids in the channel. Also, the random and complicated movements of air bubbles, created by the temporal trapping of air bubbles in the air bubble-trapping structure and by the release of them that is followed by the temporary free flow thereof, increase the stirring effect furthermore.

As explained herein before, the mixing channel of the mixer contains several kinds of liquids and air bubbles. The mixing device according to the present invention will facilitate the mixing of liquids with air bubbles.

Figure 6:
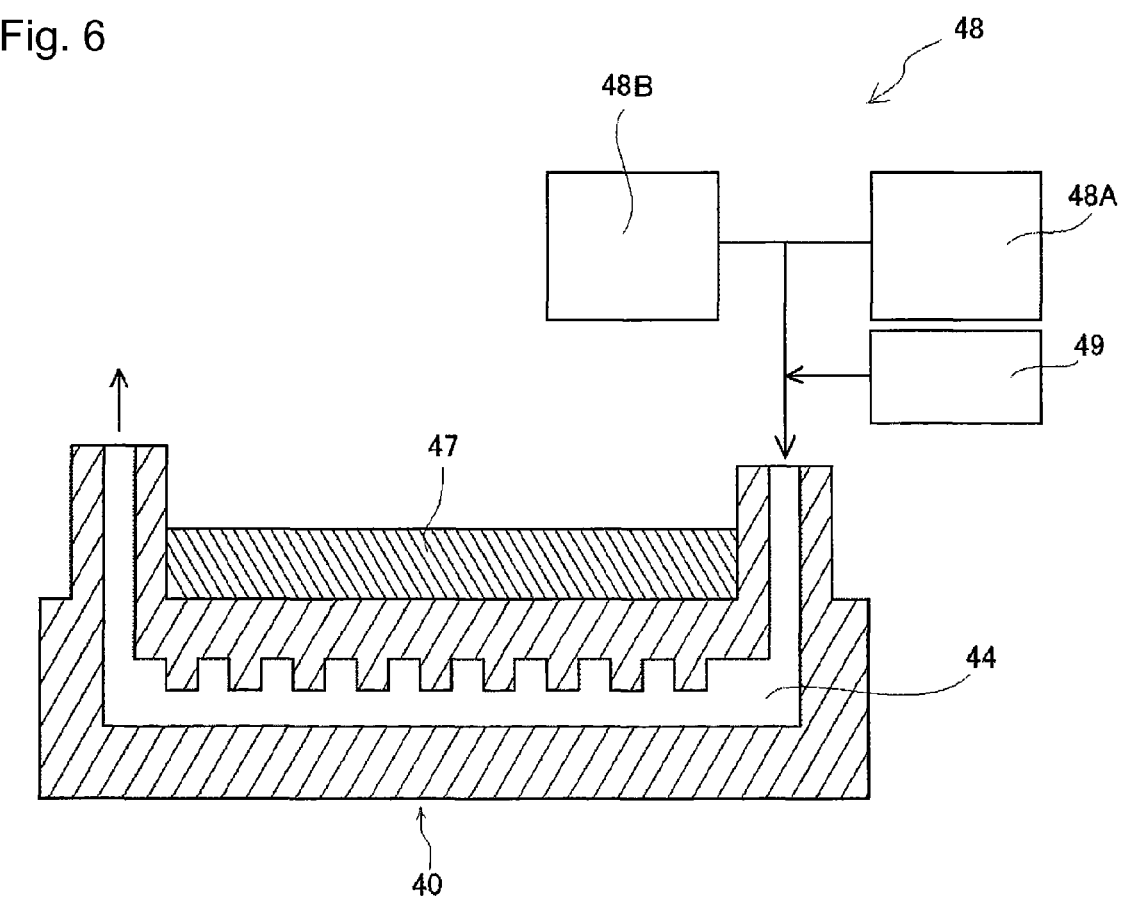
FIG. 6 is an illustration showing a mixing device, which is an example of the present invention.

As shown in FIG. 6, the mixing device has a mixer 40, which is an example of the present invention, an air bubble generator 47 for generating air bubbles in a mixing channel 44 of the mixer, and a liquid supplier 48 for supplying several kinds of liquids to be mixed one by one or simultaneously to a liquid inlet 42.

A preferable example of the air bubble generator 47 is an ultrasonic vibrator that provides liquids in the mixing channel 44 of the mixer 40 with ultrasonic vibration to generate air bubbles. It is not necessary to forcibly generate air bubbles in the liquids in the mixing channel 44, as long as air bubbles are in the channel 44. Alternatively, gas may be supplied to the liquid inlet 42 at intervals. Also, air bubbles may be forcibly supplied. In order to supply air bubbles to the liquid inlet 42, the liquid supplier 48 may be so combined with an air bubble generator 47 that ultrasonic vibration can be applied to liquids stored in or flowing through the liquid supplier 48. An air bubble supplier 49 may be employed in place of the air bubble generator 47. The air bubble supplier 49 may have various structures, such as the combination of a fan and a gas duct, as long as gas is sent to the liquid inlet 42 continuously or discontinuously.

The liquid supplier 48 has a first liquid supplying instrument 48A for supplying at least one liquid that is prone to gel or solidify, and a second liquid supplying instrument 48B for supplying at least one liquid that is prone to gel or solidify or a liquid without such tendencies. The liquid supplier 48 is not limited to the one that supplies two kinds of liquids; it may be a supplier that supplies three or more different liquids.

The mixing device is capable of mixing a liquid that is prone to gel or solidify with other liquids quickly.

The mixer or the mixing device that I have explained hereinbefore may be incorporated into a medical component-measuring unit, or a biological component-measuring unit.

A biological component-measuring unit, or a medical component-measuring unit according to the present invention, is so formed that it is capable of measuring biological components, whose measurement is necessary for medical practice, and it enables the operator to make a medical support device ready for operation efficiently and hygienically.

The biological components, the qualitative or quantitative analysis of which is necessary for medical practice, may include glucose, urea, uric acid, lactose, sucrose, lactate, ethanol, glutamic acid, ammonia, creatinine, and oxygen. Medical practice may sometimes require measurement of other properties, such as the pH value and the oxygen concentration, of body fluids. In the context of the present invention, the term "biological components" includes properties such as the pH value and the oxygen concentration.

A medical support device is a device necessary for medical doctors and veterinarians to understand the condition of a living thing accurately. Examples of medical support devices include artificial endocrine pancreas devices for supplying insulin to living things, dialyzers for dialyzing, urea concentration meters for measuring the urea content included in the body fluids of a living thing, uric acid concentration meters for measuring a uric-acid content in the body fluids of a living thing, sugar concentration meters for measuring sugar such as lactose and sucrose in the body fluids of a living thing, lactic acid concentration meters for measuring lactic acids such as lactate, glutamic acid concentration meters for measuring the glutamic acid content in the body fluids of a living thing, ammonia concentration meters for measuring an ammonia content in the body fluids of a living thing, and creatinine concentration meters for measuring a creatinine content in the body fluids of a living thing.

These various medical support devices are necessary to take exact medical action. The present invention relates to a biological component-measuring unit by which the clinical examiner is able to make a medical support device ready for operation efficiently and hygienically. For the biological component sensor, included in the unit, to measure a biological component may be employed various sensors depending on the kinds of biological components to be measured.

Examples of such biological component sensors, which may sometimes be called "biosensors" hereinafter, include enzyme sensors utilizing enzymes, microorganism sensors employing microorganisms, and hybrid sensors utilizing enzymes and microorganisms.

The enzyme or microorganism immobilized in such a biosensor is selected depending on the target to be measured, or the biological component. For example, when the target to be measured is glucose, β-D-glucose oxidase or *Pseudomonas fluorecens* may be employed as biosensor. When the target is urea, urease may be employed as biosensor; when the target is uric acid, uricase may be employed; for lactate may be used lactate oxidase; for lactose may be employed lactase or β-galactosidase; for ethanol may be employed alcohol oxidase or *Trichosporon brassicaes*; for glutamic acid may be employed glutamate dehydrogenase or *Escherichia coli*; and for ammonia may be employed nitrifying bacteria.

The medical support device equipped with the biological component measuring-unit according to the present invention is capable of dealing with one or more measurable biological components. When two or more biological components are measured, the unit should be equipped with two or more biosensors in the biological component-measuring channel. Another way to measure several components may be to make the biological component-measuring channel branch off and to connect each branch channel with one or more biosensors.

Attaching the biological component-measuring unit to a medical support device proper makes the device ready for operation.

Once attached to a medical support device proper equipped with a sensor, the substrate of the biological component-measuring unit is fixedly provided with fluid channels capable of forcibly or actively transferring body fluids in one direction and at a constant flow rate in cooperation with the fluid transfer structure fixed to the medical support device proper. The fluids flowing in the fluid channels may include body fluids sampled from a living thing, such as blood, urine, lymph and cerebrospinal fluid, mixtures of such body fluids and other liquids such as physiological saline or diluents, gas such as air, mixed fluids of gas and at least one liquid, calibrating liquids for calibrating the biosensors, and waste liquids discharged after the measurement. In this specification I sometimes call these various liquids, gas, and mixtures of liquids and gas "fluids" in general. However, a person skilled in the art to which the present invention belongs will easily understand which liquid(s), gas or mixture is meant by a general term "fluid" in the context.

On the substrate of the biological component-measuring unit may be arranged at predetermined locations, in addition to the fluid channels, fluid-contacting members and parts, which members and parts are not mounted on the medical support device proper but necessary to operate the medical support device. The medical support instrument kit according to the present invention is made by arranging these members and parts as well as the fluid channels on the substrate.

Examples of the members and parts that directly contact fluids may include an indwelling needle, a catheter, a physiological saline storage tank, a physiological saline-drawing pipe for drawing physiological saline from the tank, an inlet for introducing the physiological saline drawn through the physiological saline-drawing pipe to a catheter, a diluent storage tank in which various diluents, such as buffer solutions, which are added when necessary, are stored, diluent-drawing pipes for drawing a diluent from the diluent storage tank, diluent-supplying channels for sending the diluent to the fluid transfer structure, a calibrating liquid storage tank in which a calibrating liquid for calibrating the biosensors is stored, a calibrating liquid-drawing pipe for drawing the calibrating liquid from the calibrating liquid storage tank, a calibrating liquid-transferring channel for sending the calibrating liquid to the fluid transfer structure, a waste liquid storage tank in which waste liquid discharged from the biosensors is stored, and other members and instruments that may contact biosensors and/or fluids according to circumstances. In summary, the fluid-contacting members and parts include all such members that are not part of the medical support device proper but necessary to make the medical support device ready for operation once the biological component-measuring unit with those fluid-contacting members is attached to the medical support device proper.

I will describe the invention in more detail by explaining a glucose-measuring unit as an example of the biological component-measuring unit, and an instrument kit for an artificial endocrine pancreas device as an example of the instrument kit for a medical support device, which instrument kit is equipped with the fluid-contacting members and parts that are not mounted on the medical support device proper but necessary to the biological component-measuring unit and further to the medical support device.

Figure 9:
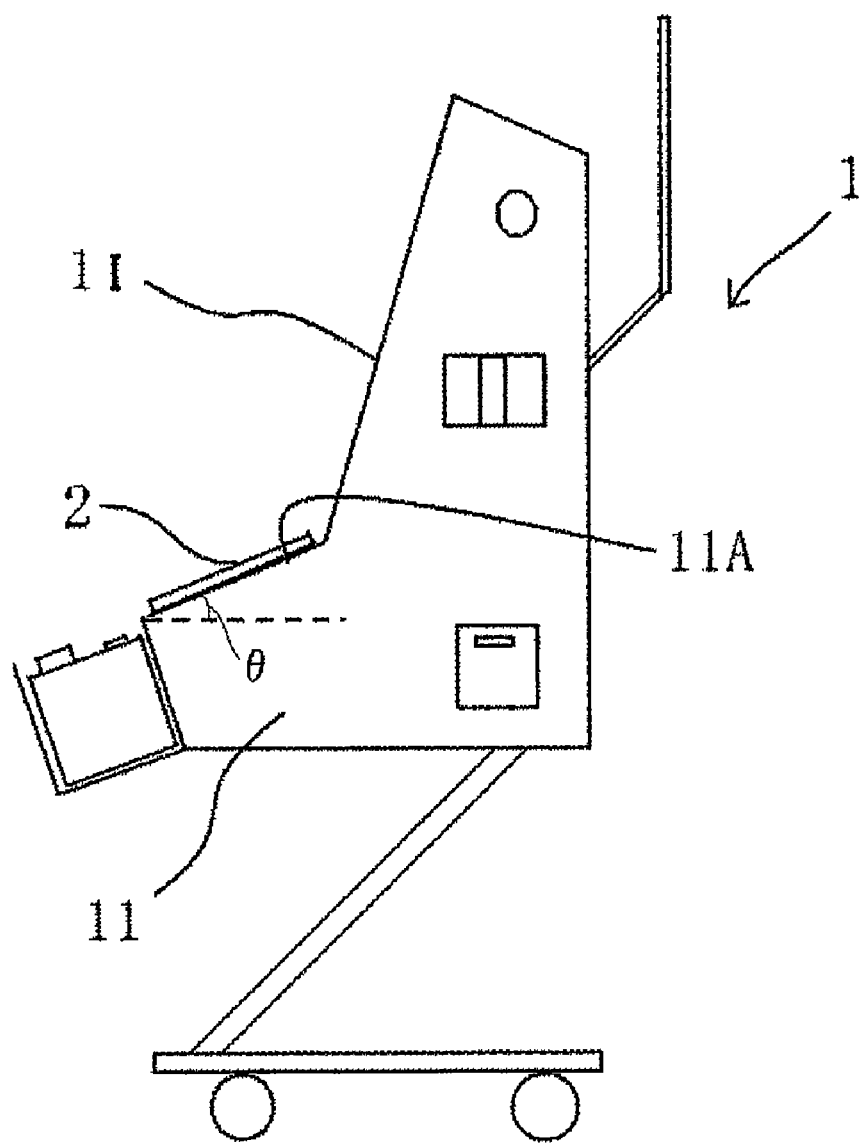
FIG. 9 is a schematic illustration showing an artificial endocrine pancreas device proper to which a blood sugar level-measuring unit is attached.

FIG. 9 shows an artificial endocrine pancreas device proper 1, which is an example of the medical support device proper. A blood sugar level-measuring unit 2, which is an example of the biological component-measuring unit according to the present invention, is attached to the artificial endocrine pancreas device proper 1. The artificial endocrine pancreas device proper 1 has a front portion 1I for operation of the device, and a mount table 11 that horizontally projects from the front portion 1I toward the operator.

The mount table 11 should be so positioned that the operator can comfortably operate it with his/her hands without bending himself/herself when s/he stands in front of the device proper. When the operator operates it in a standing posture, the mount table 11 should preferably have a mounting face 11A that is inclined upward from the operator to the front portion 11 of the artificial endocrine pancreas device. Although there is no limitation on the shape of the mounting face 11A, this embodiment employs a rectangular shape for it. The angle θ at which the mounting face 11A is inclined, or the angle θ made by the mounting face 11A and the lower end horizontal line thereof should be from not less than 60 degrees to not more than 80 degrees. When the mounting face 11A is inclined at an inclination angle within the range specified above, gas bubbles in various fluid channels fixed to the substrate that will be attached to the mounting face 11A can be moved upward, which makes it possible to separate gas from the fluids. This inclination also provides the operator with a good view of the substrate and good operability. For smooth operation by operators with different heights, the mount table 11 may be designed so as to move upward and downward with a device such as a lifting gear, whereby the blood sugar level-measuring unit 2 can be set vertically at a level of each operator's eyes or a location that enables each operator to operate the device with his/her hands smoothly.

The mount table 11 is provided with a fluid transfer structure, which is described hereinafter, and fluid channel make-and-break switches such as a first flow path changeover switch and a second flow path changeover switch.

Figure 12:
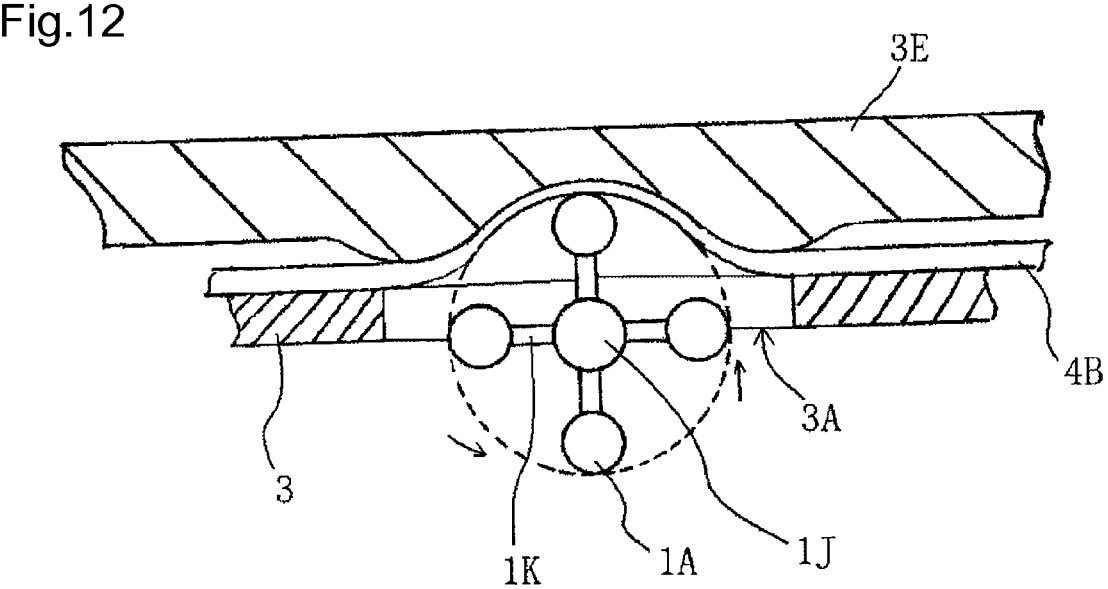
FIG. 12 is a schematic illustration showing the sectional structure of a part around the window for rollers of the blood sugar level-measuring unit, which is an embodiment of the present invention.

The fluid transfer structure of the present invention may include various structures, as long as it has a mechanical structure capable of transferring fluids in the fluid channels in one direction in cooperation with the fluid channels of the blood sugar level-measuring unit 2. Furthermore, the fluid transfer structure may take various mechanical structures, as long as it is provided with various mechanical structures with the function capable of making and breaking fluid flow in the fluid channels in cooperation with various fluid channels such as the glucose-measuring channel in the blood sugar level-measuring unit 2. One example of the fluid transfer structure that works in cooperation with the blood sugar level-measuring unit 2 in this embodiment is such that the means has a structure capable of exerting physical actions to the fluids, which actions transfer fluids such as blood, a diluent such as a buffer, and waste liquid to predetermined parts. A specific example is, as shown in FIG. 12, a squeezing roller comprising rollers 1A for squeezing elastic and flexible pipes, such as a pipe for a blood transferring channel 4B, sticks 1K for supporting these rollers 1A, a rotor 1J for supporting the sticks 1A connected thereto, and a holding plate 3E, which squeezing roller provides the channel with squeezing actions. The rotor 1J of this squeezing roller rotates around the axis thereof, which, in turn, rotates the rollers 1A around the rotor 1J. The rotation of the rollers results in the squeezing of pipes such as a pipe for the blood transferring channel 4B. A device comprising a flexible pipe, and a combination of rollers 1A, sticks 1K, a rotor 1J and a holding plate 3E is called roller pump.

Other examples of the fluid transfer structure whose structures are similar to that with the squeezing function shown in FIG. 12 are a device with a structure of the linear peristaltic pump except the tube for transferring fluid, and a device with a structure of the rotary peristaltic pump except the tube for transferring fluid. Another specific example, other than those with the squeezing function, may be a fluid transfer structure with a pressing function illustrated in FIG. 13.

Figure 13:
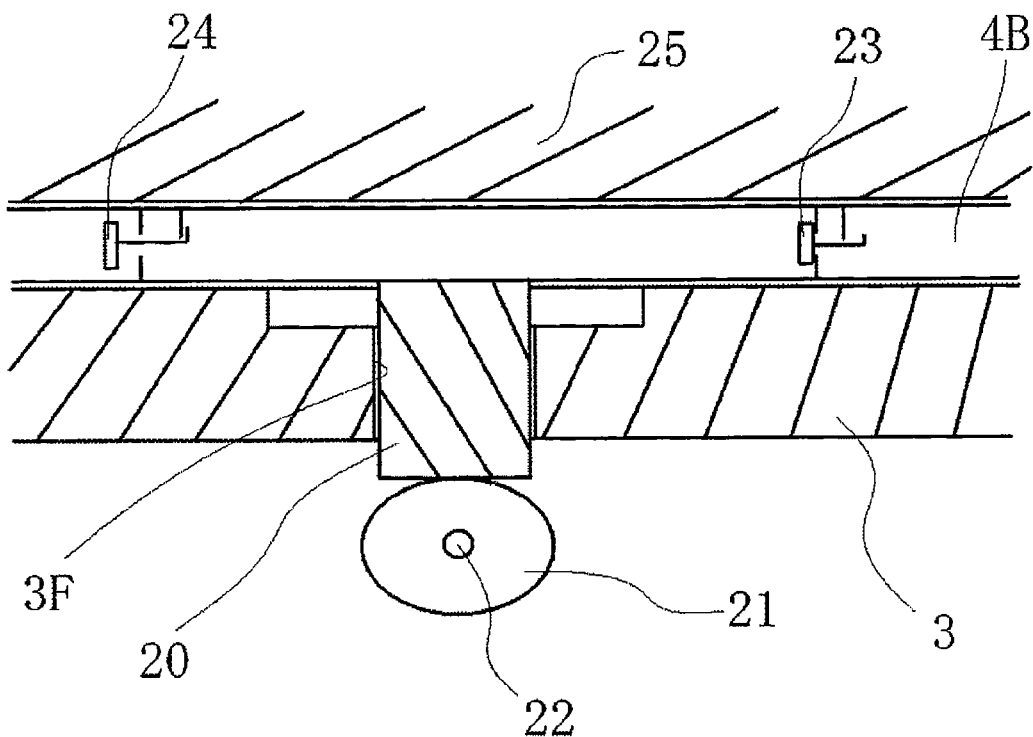
FIG. 13 is an illustration showing another example of the fluid transfer structure.

The fluid transfer structure with a pressing function comprises, as shown in FIG. 13, a pressing member 20 capable of projecting from and sinking under the upper face of the substrate 3 of the blood sugar level-measuring device 2 through a hole 3F pierced in the substrate, and an eccentric rotating cam 21 capable of rotating with keeping one end of the pressing member 20 contacted. When the eccentric rotating cam 21 rotates around its rotating shaft 22, the pressing member 20 translates the rotation into such a linear reciprocating motion that the member projects from the upper face of the substrate and sinks under it repeatedly through the hole 3F. On the other hand, each of the fluid channels, such as a blood-transferring channel 4B, is provided with a first poppet valve 23 and a second poppet valve 24 inside the channel, as described hereinafter. Reference numeral 25 denotes a holding plate to hold the fluid channel. The compression of the channel by the pressing member 20 makes smaller the volume of the space inside the channel delimited by the first poppet valve 23 and the second poppet valve 24. As a result, the first poppet valve 23 is closed while the second poppet valve 24 is opened, which makes the fluid in the delimited space flow out through the second poppet valve 24. The pressing member 20 starts retracting after the volume reaches the minimum. When the volume returns to its maximum, the first poppet valve 23 becomes opened while the second poppet valve 24 becomes closed, which invites an inflow of the fluid into the delimited space through the first poppet valve 23. Through the linear reciprocating motion of the pressing member 20, or the repetition of the upward-and-downward movement, the inflow of the fluid into the delimited space and the outflow thereof from the space are repeated alternately and the fluid is forcibly or positively transferred through the fluid channel. Since the fluid transfer structure shown in FIG. 13, in cooperation with the fluid channel, makes the fluid flow into and out of the delimited space repeatedly, it can be said that the fluid transfer structure and the fluid channel provided with valves such as the poppet valves make sort of a pump. Therefore a mechanism providing a pumping function in cooperation with a fluid channel may also be included in the fluid transfer structure of the present invention, fixed to the mount table of the artificial endocrine pancreas device proper.

For the fluid transfer structure of the artificial endocrine pancreas device proper 1, which is an embodiment of the present invention, is employed a multiple roller device having a single rotating shaft, and several elongated rollers supported by the shaft with their axes parallel to the axis of the rotating shaft. The fluids in all the fluid channels through which the fluids must be transferred are forcibly transferred by the squeezing action of the elongated rollers. The flow rate of the fluid transferred in the fluid channel per unit time period is decided by the unit sectional area of a fluid channel. In other words, the flow rate of the fluid transferred through the squeezing by the multiple roller device may be adjusted by appropriately adjusting the inner diameter of the fluid channel.

Figure 7:
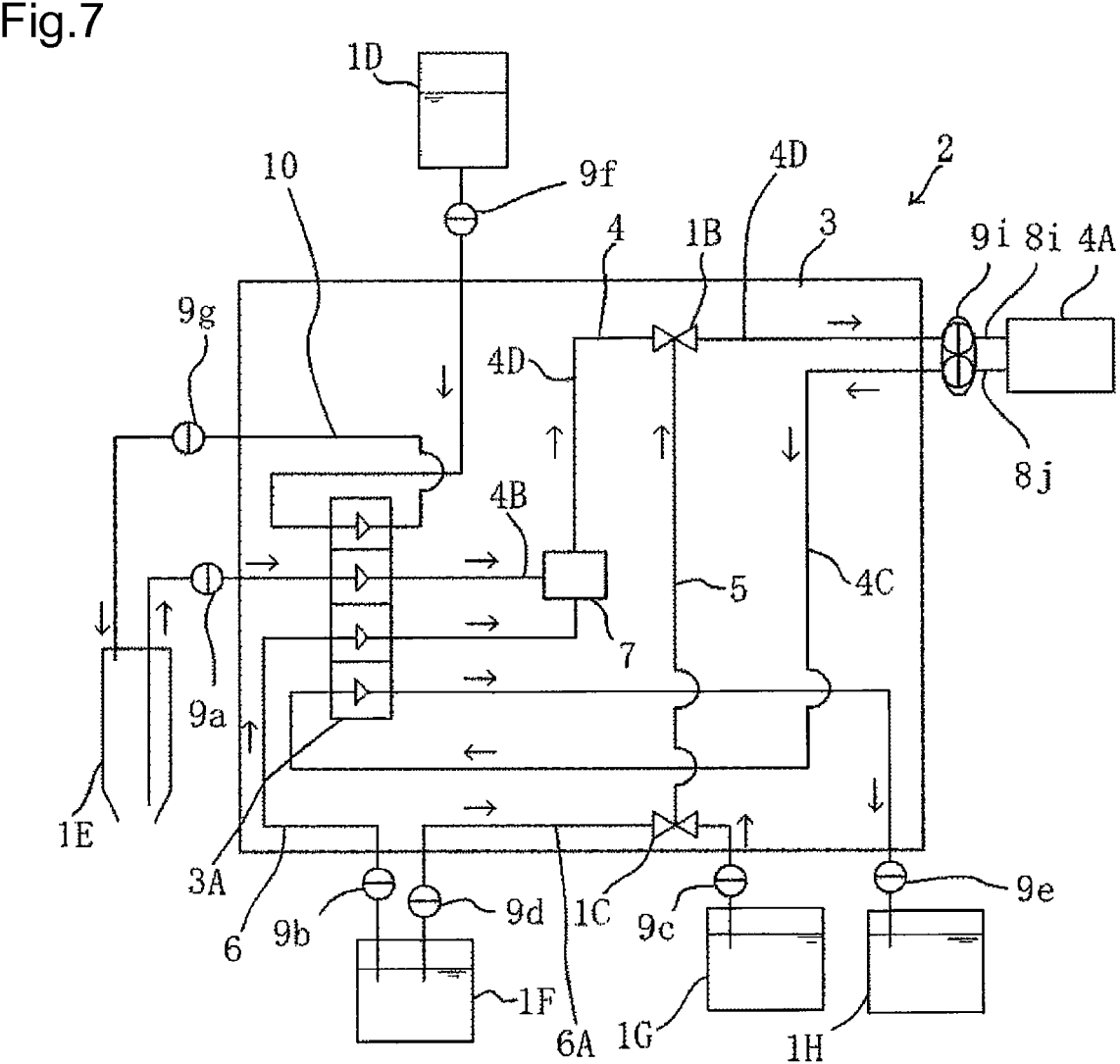
FIG. 7 is a schematic block diagram showing a blood sugar level-measuring unit, which is an example of the present invention.

As shown in FIG. 7, the blood sugar level-measuring unit 2, which is an embodiment of the present invention, is provided with a substrate 3, a glucose-measuring channel 4, which is an example of the fluid channels and the biological component-measuring channel, a calibrating liquid-supplying channel 5, which is another example of the fluid channels, a diluent-supplying channel 6, which is still another example of the fluid channels, and a mixing gadget 7.

There is no special limitation on the material of the substrate 3, as long as those various fluid channels can be fixed to the substrate. In this embodiment is employed a hard synthetic resin. Soft and flexible synthetic resins may be used depending on the situations. Specific examples of the material for the substrate 3 are a sheet made of PVC, a hard film of hard PVC or PET, and a soft PVC to which PVC tubes are easily stuck. Although the substrate 3 may be produced by machining a raw material plate, the production by molding is preferable from the viewpoint of the price of the material, a reduction of waste material such as chips from the machining, and easiness of the mass production. For the molding should be used a method suitable for production in a medium or large quantity, such as compression molding or injection molding.

On the other hand, the fluid channels fixed to the substrate 3 may be made of soft and flexible synthetic resins as well.

The fluid channels may be made of materials that are the same as the materials for the substrate 3.

The fluid channels, which may sometimes be called "tubes" hereinafter, may be fixed to the substrate, or the base, by fixedly arranging them at predetermined locations on the substrate. The substrate and the fluid channels may be separate entities, or may be a single integral entity. The substrate and integral fluid channels, or the single integral entity made by integrating the fluid channels into the substrate may be made by a die slide injection, often abbreviated to DSI, which is a precision molding by which the hollow tubes and the substrate are integrally molded. The DSI method does not require the sticking of the tubes after arranging them on the substrate. Still another method that may be utilized to prepare the substrate and integral fluid channels is fusible core injection molding in which tubes, each with a core inside it, are molded and the cores are melted away, whereby hollow tubes are prepared. The substrate 3 should preferably be made of an elastic soft material so that the substrate will have a certain dimensional tolerance.

Figure 11:
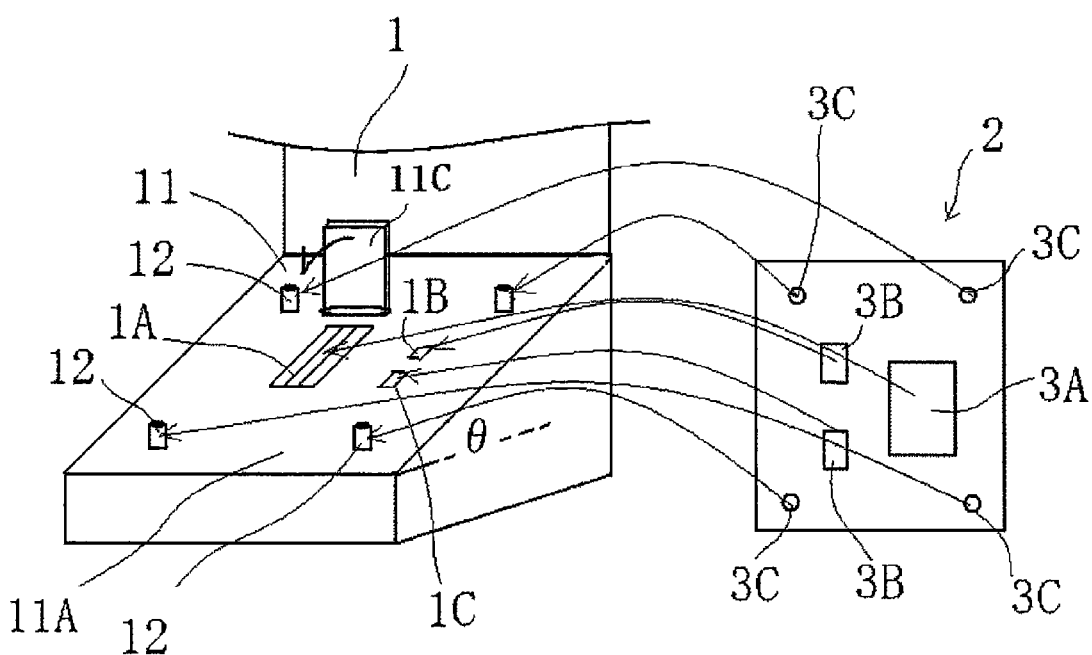
FIG. 11 is a schematic illustration showing a blood sugar level-measuring unit, which is an example of the present invention, and a mount table of an artificial endocrine pancreas device proper to which the blood sugar level-measuring unit is attached.

As shown in FIG. 11, the substrate 3 has holes for attachment in an appropriate location, which holes respectively receive attaching pins 12, projecting from parts around the four corners of the mounting face 11A. By inserting the attaching pins 12 into the holes, the operator can easily attach the blood sugar level-measuring unit 2 to the mount table 11. The operability of this blood sugar level-measuring unit is improved also in this respect.

These attaching pins 12 are protrusions projecting from predetermined parts of the surface of the mount table 11, as shown in FIG. 11. Design modifications may be made to the mechanism for attaching the substrate to the mount table.

Figure 10:
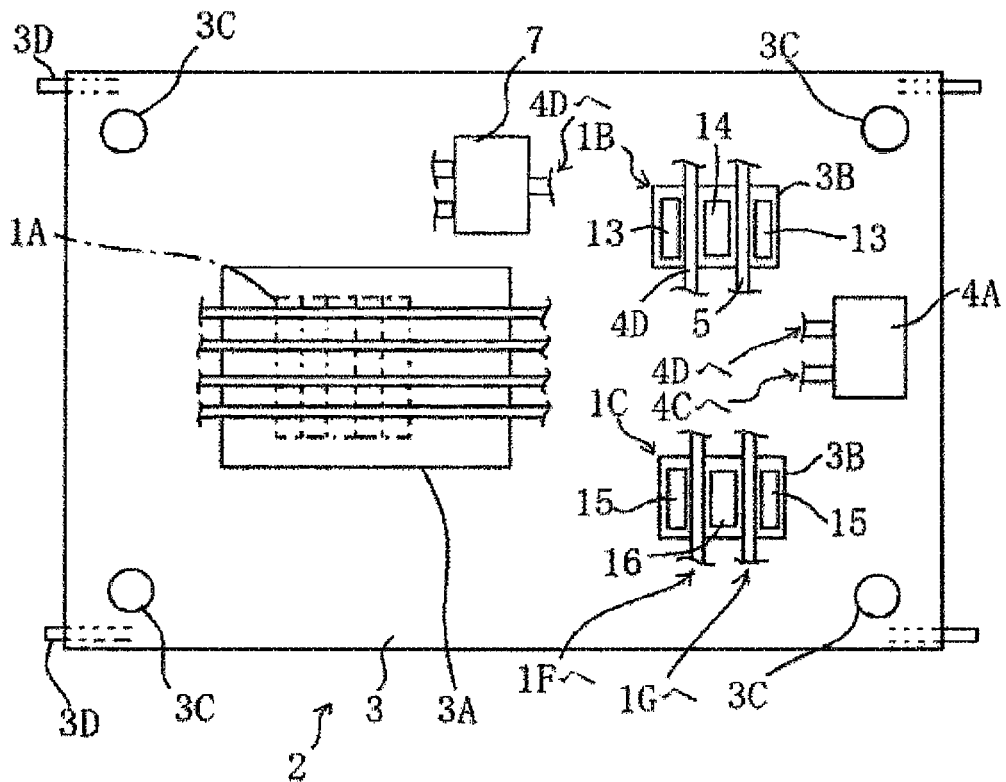
FIG. 10 is a schematic illustration showing a substrate of a blood sugar level-measuring unit, which is an example of the present invention.

As an example of a design modification, shown in FIG. 10, two attaching rods 3D are respectively fixed to first and second edges of the substrate 3. The first edge corresponds to the upper edge and the second edge to the lower edge when this substrate 3 is attached to the mount table 11. The substrate 3 may be detachably attached to the mount table 11 by making the attaching rods 3D abut on the attaching pins 12. In order to fix the attaching rods 3D to the substrate 3, each of the upper and lower edges are incurvated so as to form a hollow cylinder, into which each attaching rod 3D is inserted.

Figure 22:
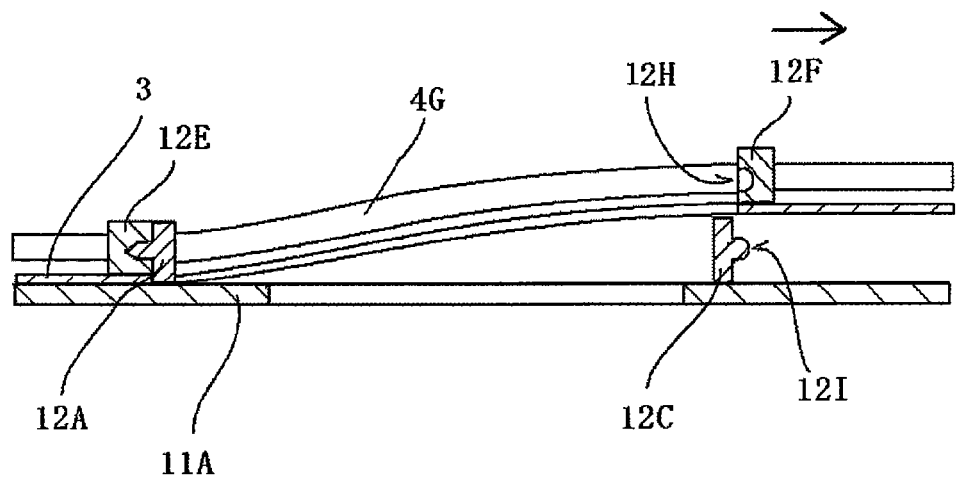
FIG. 22 is a sectional view showing the state in which the tube holders that have not been engaged yet are being drawn up to a second pair of attaching pins, which have not been engaged yet, either, and the holders are about to be engaged with the second pair of attaching pins, which follows the state shown in FIG. 21.
Figure 23:
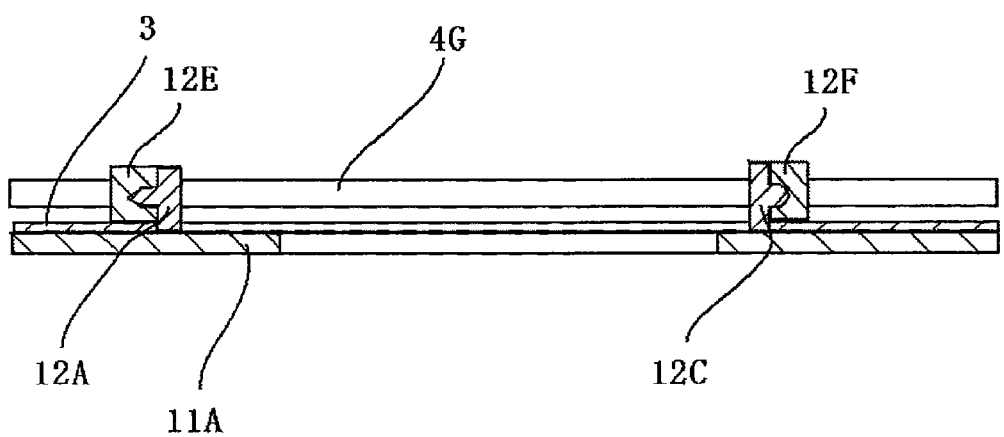
FIG. 23 is a sectional view showing the state in which the tube holders are completely engaged with the attaching pins.
Figure 24:
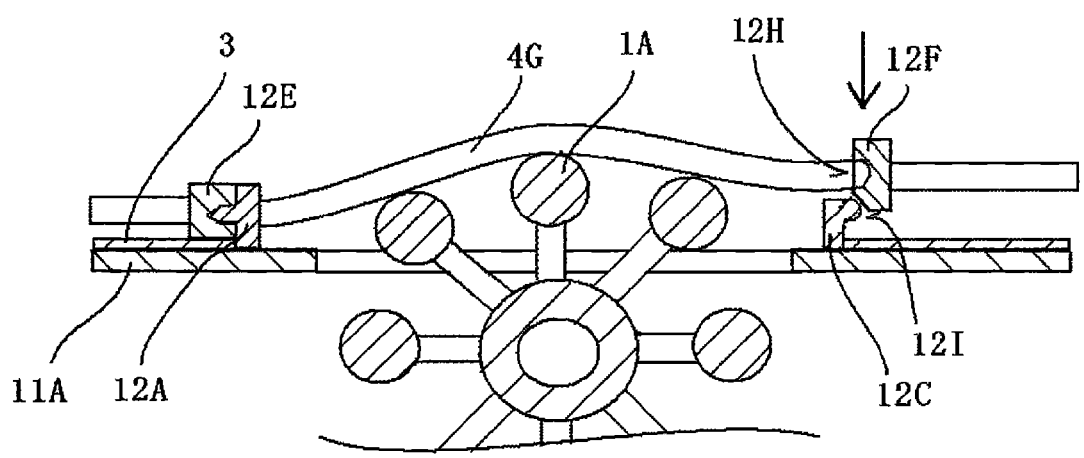
FIG. 24 is a sectional view showing the same state as that in FIG. 22, except that part of the shape of the attaching pins and part of the shape of the tube holders are different from those in FIG. 22 and the figure includes part of the rollers.

Another design modification is the attaching way shown in FIGS. 18-23. The tubes 4G running across a window 3A of the substrate 3 are provided with a tube holder 12E at a part upstream of the window 3A and another tube holder 12F at a part down stream thereof. The tube holders 12E, 12F are secured to the tubes 4G by appropriate means such as sticking, and both or one of the tube holders is also secured to the substrate 3. Notches or recesses are formed in each of the tube holders 12E, 12F respectively at such a location in proximity to one end thereof and such another location in proximity of the other end thereof that the notches or recesses formed in one tube holder respectively face the ones formed in the other tube holder. The recesses in the tube holders 12E and 12F are named engaging recesses 12G and 12H respectively. The shapes of the engaging recesses 12G, 12H should be complementary to the shapes of the projections of the attaching pins so that each projection will be tightly engaged with its paired engaging recess. On the mount table 11 onto which the substrate 3 will be attached are arranged attaching pins with projections at such locations that engaging recesses 12G, 12H should be engaged with projections of those attaching pins 12A, 12B, 12C, 12D. The distance between the attaching pins should be so adjusted that the tube will not hang slack and the substrate 3 will be settled by the two tube holders once the projections of the attaching pins engage with the engaging recesses 12G, 12H. The projections of the attaching pins located at the side where the first engagement is carried out, or those of the attaching pins 12A, 12B in FIG. 18, each may have such a shape that the projection tightly engages with the engaging recess of the tube holder 12E. One example of the shape is a slightly elongated cylinder with a pointing tip. The projections of the attaching pins 12C, 12D, located at the side where the following engagement is carried out, each may have such a shape as to enable the operator to draw the second engaging recesses 12H of the tube holder 12F over the second set of attaching pins, and to set the projections into the recesses by holding the tube holder down to the attaching pins. Examples of the shape may include a relatively short cylinder with a round tip, and a general hemisphere. The combination of the tube holders 12E, 12F and the projections of the attaching pins 12A, 12B, 12C, 12D makes it possible to easily attach the substrate 3 to or detach it from the mount table 11. This combination is advantageous, especially because the tubes and/or the substrate hardly slip off even when the tubes are squeezed by the rollers 1A. Also, FIG. 24 is a sectional view showing another embodiment in the same state as that in FIG. 22, except that the shape of the tube holder 12F and that of the projection 12C are different from those in FIG. 22. FIG. 24 includes part of the rollers 1A, which functions as a rotary peristaltic pump, and the figure also shows the shape of a tube 4G under the squeezing force. In the embodiment shown in FIG. 24, the lower corner of the tube holder, which corner contacts the attaching pin 12C, is beveled so as to form a guide. This bevel enables the operator to easily engage the engaging recess 12H of the tube holder 12F with the projection I of the attaching pin 12C just by pushing the tube holder downward. The tension of the tube 4G prevents the tube holder 12F from disengaging easily. The guide is not limited to the bevel but may be a curved face.

Figure 18:
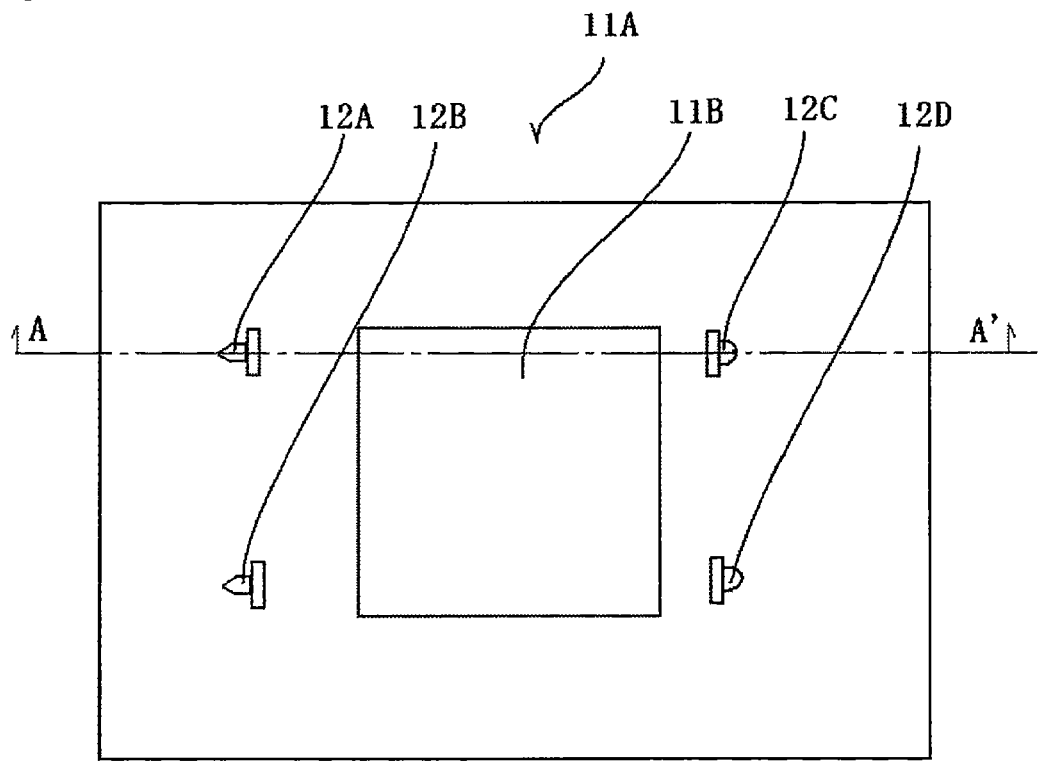
FIG. 18 is a plan view showing a part of the mount table around the opening for rollers, of an artificial endocrine pancreas device proper.
Figure 19:
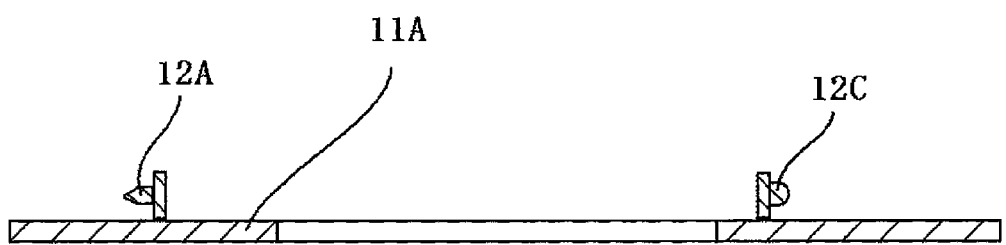
FIG. 19 is a sectional view taken along line A-A' in FIG. 18.
Figure 20:
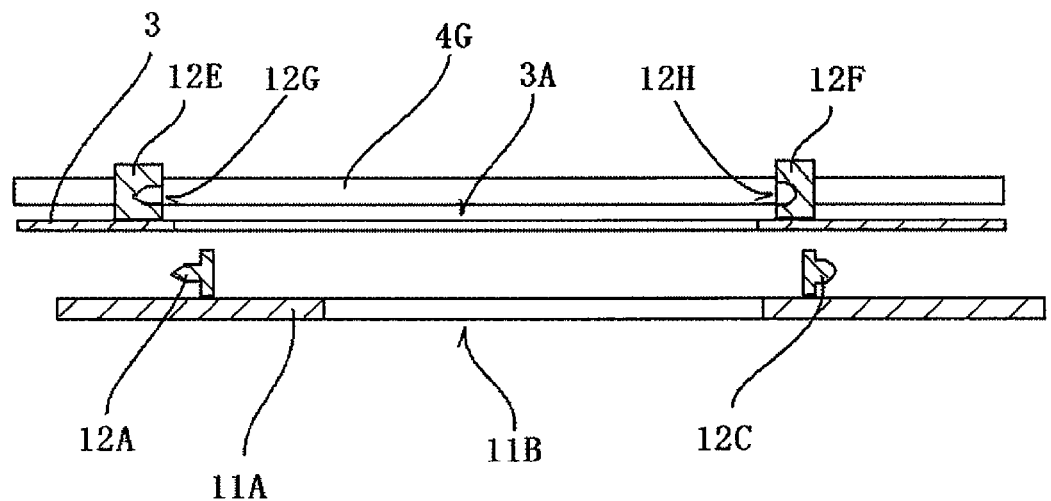
FIG. 20 is a sectional view, shown in the same way as in FIG. 19, illustrating the part of the mount table around the opening for rollers, of the artificial endocrine pancreas device proper over which the substrate to be attached to the mount table is placed.
Figure 21:
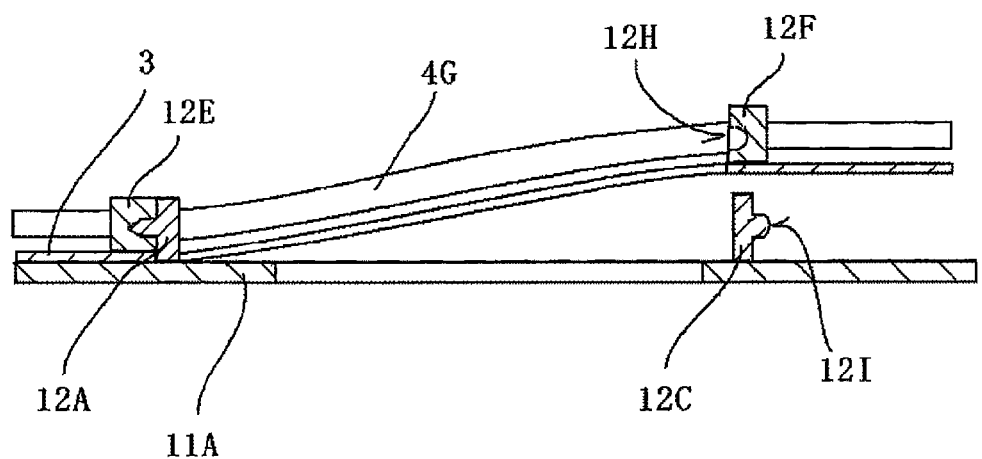
FIG. 21 is a sectional view showing the state in which the tube holders at one side are engaged with a first pair of attaching pins, which follows the state shown in FIG. 20.

I will explain a specific example of how to attach the substrate to the mounting face. As shown in FIG. 18, four attaching pins 12A, 12B, 12C, 12D have been arranged on the mounting face 11A of the mount table 11, around the opening 11 in which the rollers 1A are placed. In FIGS. 18-23, the rollers are not shown. The distance between the attaching pins, parallel to the running of the tubes, is such that the tube holders do not disengage from the attaching pins due to the tension of the tube when the respective projections of the four attaching pins are engaged with the engaging recesses 12G, 12H of the tube holders 12E, 12F respectively located upstream to and downstream to the window 3A of the substrate 3, across which the tubes 4G secured to the substrate run. FIG. 19 is a sectional view taken along line A-A' in FIG. 18. FIG. 20 is a fragmentary section illustrating a part of the mounting face shown in FIG. 19, the part being around the opening for the rollers over which the substrate 3 is placed. FIG. 21 is a sectional view illustrating the state in which the tube holder 12E is engaged with the attaching pins 12A, 12B. FIG. 22 is a sectional view showing the state in which the tube holder 12F is being drawn in the right direction in the figure, up to the projection 12I of the attaching pin 12C. Pushing the tube holder 12F downward in this state will make the tube holder engage with the attaching pins 12C, 12D. FIG. 23 illustrates the state in which the tube holder 12F is completely engaged with the attaching pin 12C and the substrate 3 is firmly set on the mounting face 11A.

As shown in FIG. 11, the substrate 3 has a window for the rollers 3A and two apertures 3B. The location of the window for the rollers 3A is so decided that the various fluid channels so disposed as to run across the window 3A will be squeezed by the rollers mounted on the mount table 11. The respective locations of the two apertures 3B are so decided that the protrusions of a first flow path changeover switch 1B and those of a second flow path changeover switch 1C will stick out from the mount table 11 through the respective apertures. The window for the rollers 3A of the substrate 3, after the substrate 3 is attached to the mount table, is held down by a lid for the opening 11C with which the mounting face 11A of the mount table 11 is provided. The lid for the opening C serves as the holding plate 3E.

This embodiment, which employs the window for the rollers 3A formed in the substrate 3, enables each roller of the multiple roller to directly contact the fluid channels such as a glucose-measuring channel and to squeeze the channels. However, as long as fluids in the fluid channels are transferred by the fluid transfer structure, it is not necessary to form such a window as the window for the rollers 3A in the substrate. When the substrate is made of a flexible thin sheet, the fluid channels may be squeezed by the rollers with this substrate that does not have the window 3A in between. The latter embodiment is advantageous when the tubes are broken, because the substrate made of a thin sheet serves as a cover with which the mount table is overlaid, and the fluids flowing out of the tubes are prevented from coming into the medical support device proper 1.

As shown in FIG. 7, the substrate 3 is equipped with a glucose-measuring channel 4, a calibrating liquid-supplying channel 5, a diluent-supplying channel 6, and a mixing gadget 7. The glucose sensor 4A is not placed in the glucose-measuring channel 4 on the substrate 3. Instead are disposed two connectors 9i that are respectively connected to a sample inlet 8i of a glucose sensor 4A provided outside the blood sugar level-measuring unit 2 and a sample outlet 8j thereof.

The glucose-measuring channel 4 is in the shape of a tube made of, for example a flexible material, so that sampled blood is transferred through the channel 4 by, for example, the rollers 1A of the fluid transfer structure via the connectors 9i to a glucose sensor 4A, which is an example of the biological component sensor. In this embodiment, the glucose-measuring channel 4 is further provided with a blood-transferring channel 4B for transferring sampled blood to a mixer 7, which is an example of the mixing gadget, a sample liquid-transferring channel 4D for transferring a blood-containing sample, a mixture of the sampled blood and a diluent made by the mixer 7, and a waste liquid-transferring channel 4C for transferring a fluid the measurement of which has been completed in the glucose sensor 4A as waste liquid.

The connectors 9i should connect the sample liquid-transferring channel 4D with the sample inlet 8i of the glucose sensor and the waste liquid-transferring channel 4C with the sample inlet 8j thereof. The two connectors may be, for example, integrated into one structure that provides two independent connections, or made separately. The connections of the fluid channels provided by the connectors should be liquid-tight, or free from leakage. Specifically, the connector 9i receiving the transferring channels, and the connector 9i receiving the sample inlet 8i and the sample outlet 8j should be contact bonded, or tightly joined with connecting elements such as bolts and nuts. From the viewpoint of operability of the blood sugar level-measuring unit 2 in practical use, the most preferable are connectors that can be attached or detached very easily just by applying a pressure by the hand. The advantageous characteristic of this embodiment lies in easily providing other measurements, such as a measurement of a pH value or a measurement of a lactic acid level, just by exchanging the glucose sensor 4A with other sensors. Also, when sensors such as a glucose sensor 4A are expensive, the operator does not have to use the sensors only once and throw them away; s/he can throw away only the blood sugar level-measuring unit 2 of this embodiment.

To one end of the blood-transferring channel 4B is attached a connector 9a that is so designed as to be detachably connected to the end of a blood-drawing channel, such as a blood sampling channel, of a blood sampling device such as a catheter. The one end of the blood-transferring channel 4B provided with the connector 9a is outside the substrate 3. Portions of the blood-transferring channel 4B other than the one end are neatly arranged on the surface of the substrate 3 together with other fluid channels, and a central portion of the channel 4B is so disposed that the portion runs across the window for the rollers 3A with tension. This embodiment employs a double lumen catheter for the catheter 1E.

As shown in FIG. 7, the sample liquid-transferring channel 4D is neatly arranged with other fluid channels on the surface of the substrate 3. A part of the sample liquid-transferring channel 4D, which part is between the two ends of the channel, is so disposed that the part extends across the aperture 3B with tension, in order to be provided with the first flow path changeover switch 1B.

For the glucose sensor 4A that is connected to the glucose-measuring channel 4 may be employed, for example, a biosensor made by coating a carbon electrode with an osmium polymer, drying the coated electrode at room temperature, applying an enzyme solution thereto to make a film, and immobilizing the enzyme by a cross-linking agent such as glutaraldehyde. When this biosensor is used as the glucose sensor 4A, an oxidation reaction takes place between peroxide and a peroxidase enzyme, which is immobilized in the osmium polymer, and the reaction is followed by a reduction reaction between the osmium polymer, the peroxidase and the electrode. The electrode potential during these reactions is 0 mV compared with the electrode potential of the silver-silver chloride electrode. Therefore the utilization of the glucose oxidase for the enzyme for the oxidation reaction leads to a quick detection of glucose and an easy measurement of the concentration thereof. The glucose sensor 4A may include, other than that explained above, a glucose sensor including an osmium (II)-bipyridine complex, one including a ruthenium complex, and a glucose sensor with an electrode modified with a polypyrrole into which a tris-osmium complex is immobilized.

Among these various glucose sensors, the biosensor employing the osmium polymer is preferable. Suitable glucose sensors are film sensors having a work electrode of platinum, silver or carbon, and an enzyme film of an osmium polymer impregnated with peroxidase.

The waste liquid-transferring channel 4C is further disposed on the substrate 3. Through the waste liquid-transferring channel 4C the fluid that has been measured by the glucose sensor is discharged as a waste liquid to a waste liquid tank 1H. To one end of this waste liquid-transferring channel 4C is fixed a connector 9e that is so designed that it is capable of being detachably coupled with a connector of the inlet for discharging the waste liquid into the waste liquid tank 1H. The one end of the waste liquid-transferring channel 4C equipped with the connector 9e is outside the substrate 3. Portions of the waste liquid-transferring channel 4C other than the one end are neatly arranged on the surface of the substrate 3 together with other fluid channels. A part of the waste liquid-transferring channel 4C, which part is between the two ends of the channel, is so disposed that the part extends across the window for the rollers 3A.

As shown in FIG. 7, to the mixer 7 is connected a diluent-supplying channel 6 that supplies a diluent stored in a diluent tank 1F, which is an example of the diluent storage tank mounted on, for example, an artificial endocrine pancreas device proper, a device other than the blood sugar level-measuring unit 2.

To one end of this diluent-supplying channel 6 is fixed a connector 9b that is so designed that it is capable of being detachably coupled with a connector of a diluent outlet, or a diluent-drawing channel through which the diluent stored in the diluent tank 1F is drawn. The one end of the diluent-supplying channel 6 equipped with the connector 9b is outside the substrate 3. Portions of the diluent-supplying channel 6 other than the one end are neatly arranged on the surface of the substrate 3 together with other fluid channels. A central part of the diluent-supplying channel 6 is so disposed that the part extends across the window for the rollers 3A with tension. The other end, or the end opposite the one end connected to the connector 9b, of the channel is connected with the mixer 7.

The diluent may be any solution as long as it is capable of diluting blood that is transferred through the blood-transferring channel 4B and of keeping constant the pH value of a sample liquid to be introduced into the glucose sensor 4A. An example of the diluent is a phosphoric acid buffer, which is also called a buffer. Therefore the diluent in this embodiment can be considered to be a buffer. When a buffer is used as the diluent, the buffer keeps the pH value of a sample liquid constant, which leads to a stable measurement of a blood sugar level by the glucose sensor that has acute sensitivity to pH values.

As shown in FIG. 7, to the first flow path changeover switch 1B is connected a calibrating liquid-supplying channel 5 that supplies a calibrating liquid stored in a calibrating liquid tank 1G, which is an example of the calibrating liquid storage tank mounted on, for example, an artificial endocrine pancreas device proper, a device other than the blood sugar level-measuring unit 2, to the sample liquid-transferring channel 4D. To one end of this calibrating liquid-supplying channel 5 is fixed a connector 9c that is so designed that it is capable of being detachably coupled with a connector of a calibrating liquid outlet, or a calibrating liquid-drawing channel through which the calibrating liquid stored in the calibrating liquid tank 1G is drawn. The one end of the calibrating liquid-supplying channel 5 equipped with the connector 9c is outside the substrate 3. Portions of the calibrating liquid-supplying channel 5 other than the one end are neatly arranged on the surface of the substrate 3 together with other fluid channels. A part of the calibrating liquid-supplying channel 5, which part is between the two ends of the channel, is provided with a second flow path changeover switch 1C.

A second diluent-supplying channel 6A is connected to the second flow path changeover switch 1C. To one end of this second diluent-supplying channel 6A is fixed a connector 9d that is so designed that it is capable of being detachably coupled with a connector of a second diluent outlet through which the diluent, such as a buffer, stored in the diluent tank 1F is drawn. The one end of the second diluent-supplying channel 6A equipped with the connector 9d is outside the substrate 3. Portions of the second diluent-supplying channel 6A other than the one end are neatly arranged on the surface of the substrate 3 together with other fluid channels.

Fixed to the substrate 3 is a physiological saline-transferring channel 10 that sends a physiological saline including heparin, which may sometimes be called just physiological saline hereinafter, stored in a physiological saline tank 1D, mounted on, for example, an artificial endocrine pancreas device proper 1, a device other than the blood sugar level-measuring unit 2, to the catheter 1E.

Fixed to one end of this physiological saline-transferring channel 10 is a connector 9f that is so designed that it is capable of being detachably coupled with a connector of a physiological saline outlet through which the physiological saline stored in the physiological saline tank 1D that is mounted on, for example, an artificial endocrine pancreas device proper 1, a device other than the blood sugar level-measuring unit 2, is drawn. The one end of the physiological saline-transferring channel 10 equipped with the connector 9f is outside the substrate 3. On the other hand, to the other end of this physiological saline-transferring channel 10 is fixed a connector 9g so designed that it is capable of being detachably coupled with a connector fixed to an inlet of the catheter 1E. The other end of the physiological saline-transferring channel 10 equipped with the connector 9g is outside the substrate 3. The central part of this physiological saline-transferring channel 10, or part other than the one end and the other end, both being outside of the substrate 3, is neatly arranged on the surface of the substrate 3 together with other fluid channels, and so disposed that a portion of the part runs across the window for the rollers 3A.

The first flow path changeover switch 1B will be explained in detail in the following paragraphs.

Various mechanical structures may be employed for the first flow path changeover switch 1B, as long as they are capable of switching from state (1) in which the blood-transferring channel 4B communicates with the sample liquid-transferring channel 4D to state (2) in which the calibrating liquid-supplying channel 5 communicates with the sample liquid-transferring channel 4D, and switching from state (2) to state (1).

In the embodiment shown in FIG. 10, a branched tube such as a Y-shaped tube (not shown in the figures), is grafted in the sample liquid-transferring channel 4D; the first and second branches of the Y-shaped tube are interposed in the sample liquid-transferring channel 4D, and the third branch is connected to the calibrating liquid-supplying channel 5. The first flow path changeover switch 1B comprises, as shown in FIG. 10, a pair of first stationary members 13, 13, and a first movable member 14 disposed between the first stationary members and movable toward one first stationary member and the other first stationary member, wherein the pair of first stationary members and the first movable member stick out upward from the surface of the substrate 3 through the aperture 3B formed in the substrate 3 when the blood sugar level-measuring unit 2 is attached to the mount table 11. As understood from FIG. 4, a part of the sample liquid-transferring channel 4D, which part is located upstream of the Y-shaped tube, is disposed between one first stationary member 13 and the first movable member 14, and a part of the calibrating liquid-supplying channel 5 is disposed between the other first stationary member 13 and the first movable member 14. When the first movable member 14 moves in such a direction as to hold, for example, the sample liquid-transferring channel 4D between the one stationary member 13 and the first movable member to compress it, the sample liquid-transferring channel 4D is blocked up, whereby state (2) in which the calibrating liquid-supplying channel 5 communicates with the sample liquid-transferring channel 4D is realized. On the other hand, when the first movable member 14 moves in such a direction as to hold, for example, the calibrating liquid-supplying channel 5 between the other stationary member 13 and the first movable member to compress it, the calibrating liquid-supplying channel 5 is blocked up, whereby state (1) in which the blood-transferring channel 4B communicates with the sample liquid-transferring channel 4D is realized.

As mentioned above, the first flow path changeover switch 1B, which is an example of the fluid channel make-and-break switch, is not limited to the combination of the pair of the first stationary members 13 and the first movable member 14, as long as the switch is capable of changing the ways of the communication. For example, other valves, such as a cross valve, two 2-way valves, or a rotary valve, may be used.

One novel feature of the present invention is that the make-and-break of fluid channels can be made by the fluid channels arranged on the substrate and the fluid channel make-and-break switch with which the mount table is provided, once the substrate of a biological component-measuring unit, such as a blood sugar level-measuring unit, according to the present invention, is attached to the mount table of a medical support device proper, such as an artificial endocrine pancreas proper. Thus, the blood sugar level-measuring unit 2, which itself does not make or break the fluid channels, obtains the function of making and breaking the fluid channels when the unit is attached to the mount table. As is described below, the second flow path changeover switch 1C provides the same function as the first flow path changeover switch 1B.

The second flow path changeover switch 1C will be explained in detail hereinafter.

Various mechanical structures may be employed for the second flow path changeover switch 1C, as long as they are capable of switching from state (a) in which the second diluent-supplying channel 6A communicates with the calibrating liquid-supplying channel 5 in the section between this second flow path changeover switch 1C and the first flow path changeover switch 1B, to state (b) in which the communication through the calibrating liquid-supplying channel from the calibrating liquid tank 1G to the first flow path changeover switch 1B is established.

In the embodiment shown in FIG. 10, a branched tube such as a Y-shaped tube (not shown in the figures), is grafted in the calibrating liquid-supplying channel 5; the first and second branches of the Y-shaped tube are interposed in the calibrating liquid-supplying channel 5, and the third branch is connected to the second diluent-supplying channel 6A. The second flow path changeover switch 1C comprises, as shown in FIG. 10, a pair of second stationary members 15, 15, and a second movable member 16 disposed between the second stationary members and movable toward one of the second stationary members and the other second stationary member, wherein the pair of second stationary members and the second movable member stick out upward from the surface of the substrate 3 through the aperture 3B formed in the substrate 3 when the blood sugar level-measuring unit 2 is attached to the mount table 11. As understood from FIG. 10, a part of the calibrating liquid-supplying channel 5, which is connected to a branch of the Y-shaped tube and which runs to the calibrating-liquid tank 1G, is placed between one second stationary member 15 and the second movable member 16, while a part of the second diluent-supplying channel 6A, which is connected to the third branch of the Y-shaped tube, is placed between the other second stationary member 15 and the second movable member 16. When the second movable member 16 moves, for example, to the other second stationary member 15, and the second movable member 16 and the other second stationary member 15 pinch and compress the part of the second diluent-supplying channel 6A, the second diluent-supplying channel 6A is blocked up, which in turn realizes state (b) in which the calibrating liquid stored in the calibrating liquid tank 1G can be transferred to the first flow path changeover switch 1B. On the other hand, when the second movable member 16 moves to the one second stationary member 15, and the second movable member 16 and the other second stationary member 15 pinch and compress the part of the calibrating liquid-supplying channel 5, the calibrating liquid-supplying channel 5 is blocked up, which realizes the state (a) in which the second diluent-supplying channel 6A communicates with the section of the calibrating liquid-supplying channel 5, which section is between the second flow path changeover switch 1C and the first flow path changeover switch 1B.

As mentioned above, the second flow path changeover switch 1C is not limited to the combination of the pair of the second stationary members 15 and the second movable member 16, as long as the switch is capable of changing the ways of the communication. For example, other valves, such as a cross valve, two 2-way valves, or a rotary valve, may be used.

In the following paragraphs I will explain the mixer 7 in detail.

Figure 8:
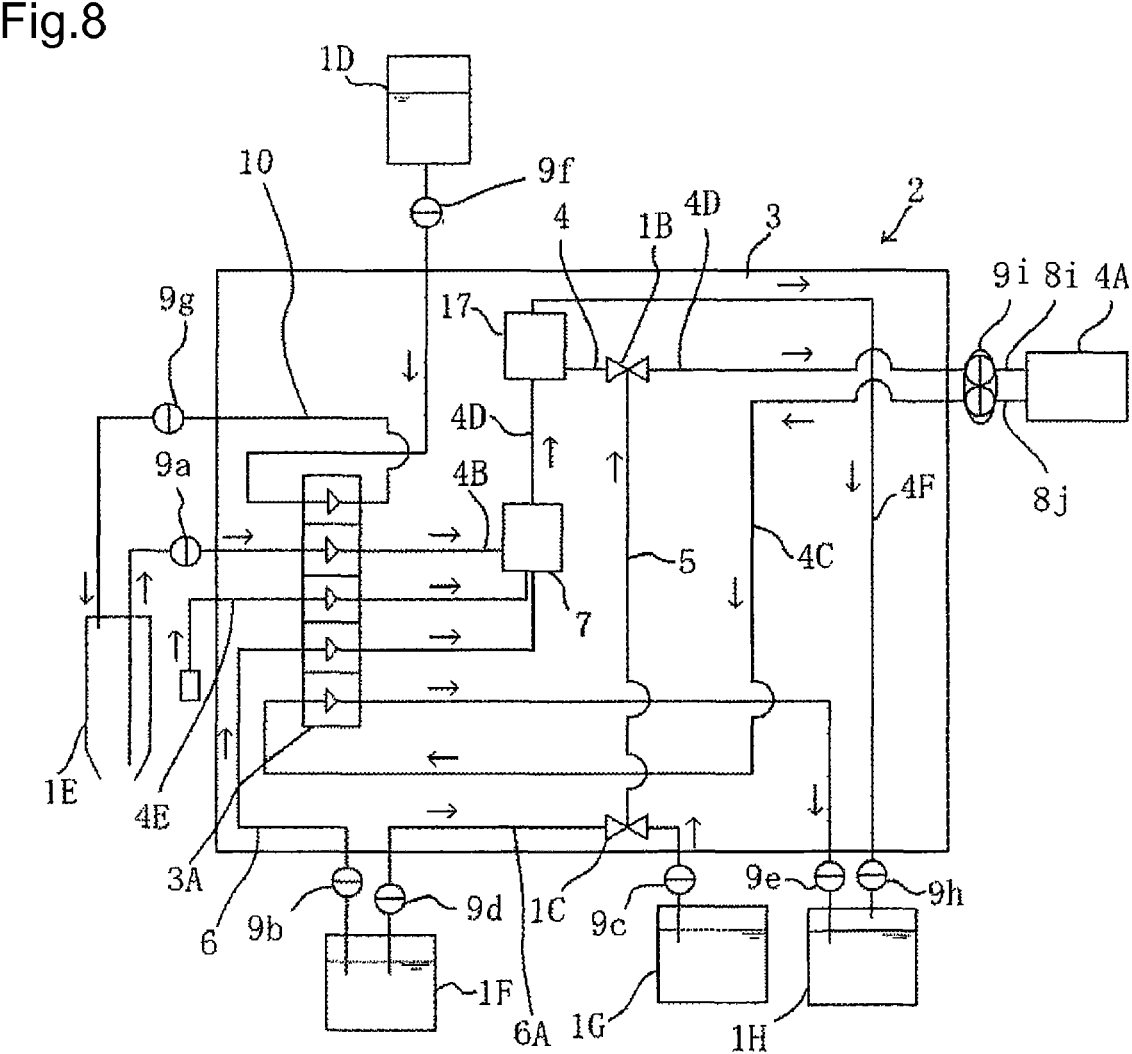
FIG. 8 is a schematic block diagram showing another example of the blood sugar level-measuring unit according to the present invention.

As shown in FIG. 8, various mechanical structures may be employed for the mixer 7, as long as they are capable of mixing blood transferred through the blood-transferring channel 4B with a diluent, for example a buffer, supplied through the diluent-supplying channel 6. Because the fluid channel between the mixer 7 and the glucose sensor 4A is short in the blood sugar level-measuring unit 2, mechanical structures capable of mixing the blood with the diluent sufficiently until the sample liquid reaches the glucose sensor 4A should preferably be employed.

Figure 14:
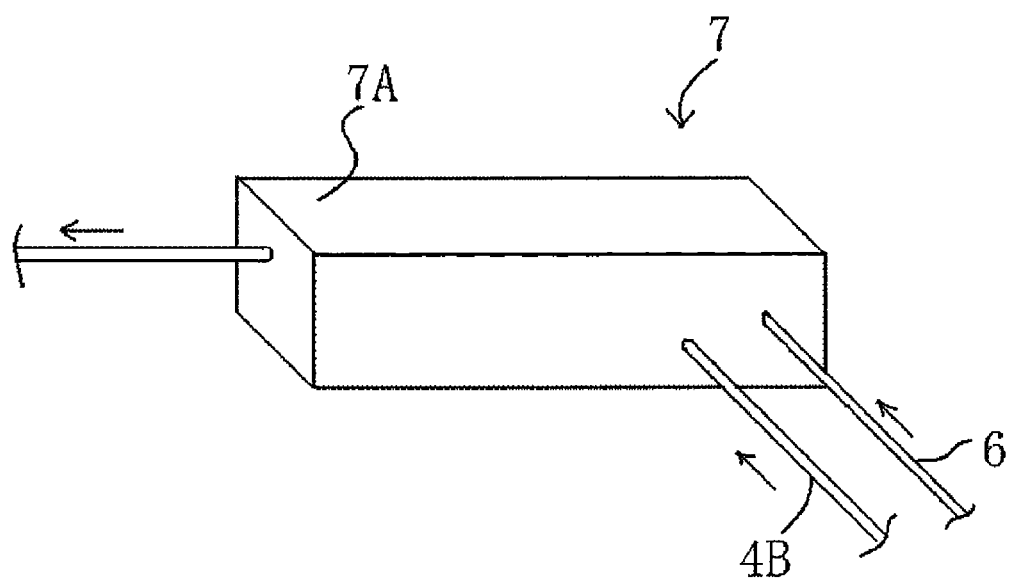
FIG. 14 is a schematic representation of a mixer of the blood sugar level-measuring unit, which is an example of the present invention.
Figure 15:
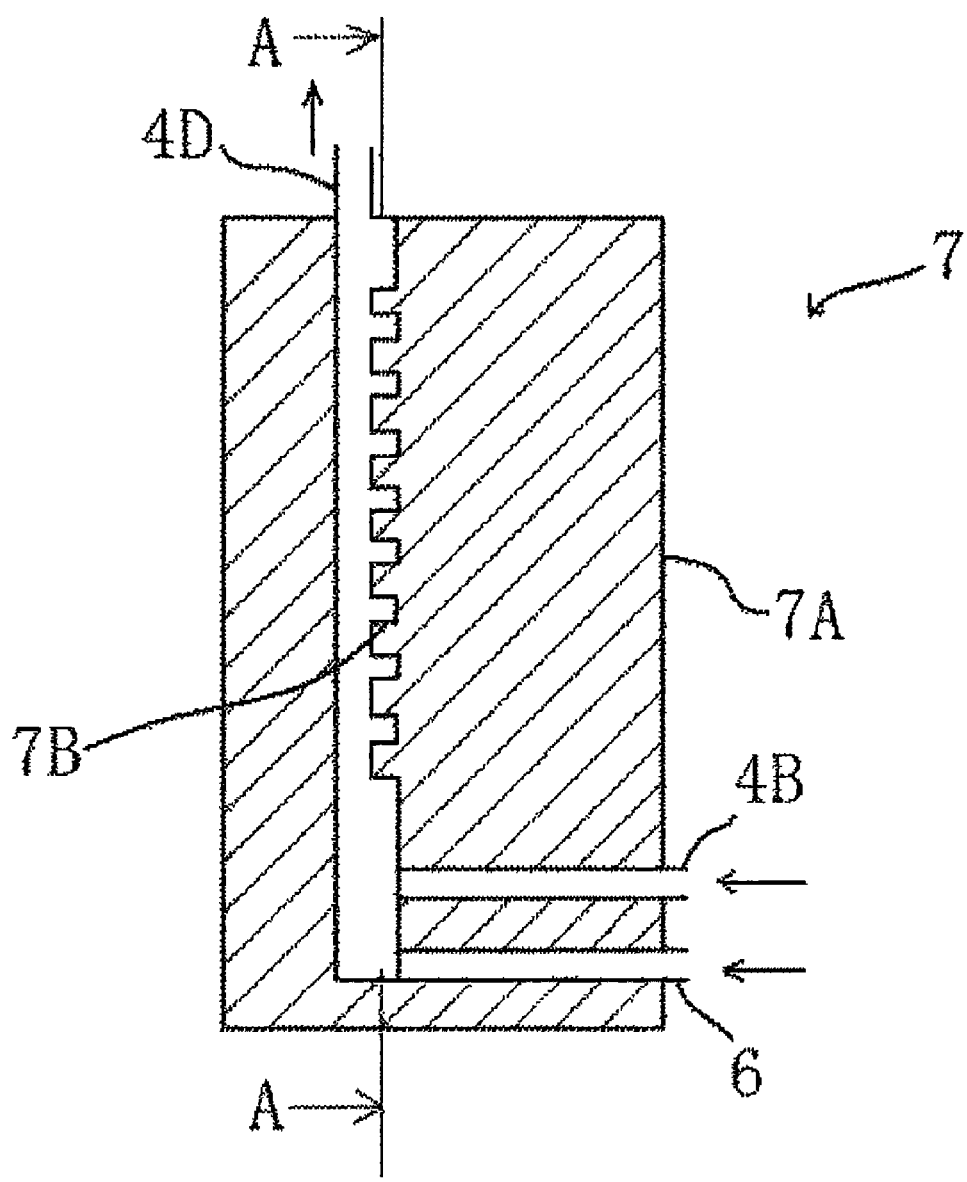
FIG. 15 is a schematic view showing the structure of a section of the mixer of the blood sugar level-measuring unit, which is an example of the present invention.
Figure 16:
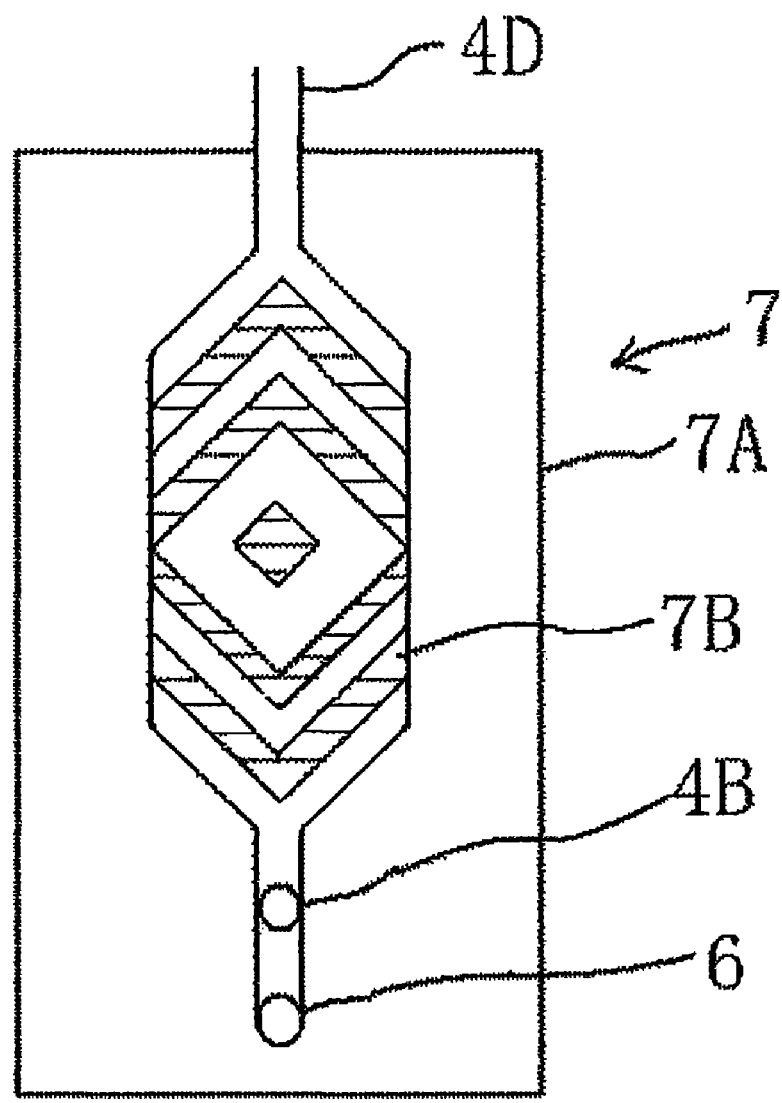
FIG. 16 is a schematic sectional view taken along line A-A in FIG. 15, showing another section of the mixer.

An example of a preferable mixer 7 may be the one with the structure shown in FIGS. 14-16.

As shown in FIGS. 14-16, the mixer 7 has a rugged part 7B comprised of continuous alternate projections and depressions running in the direction of fluid flow, which rugged part is formed in the inside face of a wall that defines, together with the other walls, an inner fluid flow space of the mixer proper 7A in the shape of a rectangular parallelepiped. The inner fluid flow space corresponds to the mixing channel 41 in FIGS. 1 and 2. As shown in FIG. 16, which is a sectional view taken along line A-A in FIG. 15, the rugged part 7B has a central portion in the form of diamonds. In more detail, the rugged part 7B has, in the direction of fluid flow, a V-shaped rugged portion comprising alternate V-shaped projections and V-shaped depressions first. In other words, the first portion of the rugged part has several V-shaped projections and several V-shaped depressions each between adjacent V-shaped projections. Next comes the central portion, which is followed by a reverse V-shaped rugged portion comprised of several projections in the shaped of a reverse V and several reverse V-shaped depressions each between adjacent reverse V-shaped projections. The diluent-supplying channel 6 and the blood-transferring channel 4B communicate with the inner fluid flow space.

Blood and a diluent introduced into the inner fluid flow space of the mixer proper 7A strike against the first projection of the rugged part 7B, which disturbs the flow of the blood and that of the diluent. The disturbed flows of the blood and the diluent climb over the first projection and fall into the adjacent depression. In the depression the next projection makes the flow of the blood and that of the diluent collide, and the flows are disturbed again. Also, the flow of the blood and that of the diluent are divided into a flow component running straight and flow components each running aslant along the walls of the V, since the rugged part 7B has the V-shaped rugged portion and the reverse V-shaped rugged portion. This division of the flows also creates disturbed flows of the blood and the diluent. The repetition of the disturbances, caused by crashes of the blood and the diluent against the projections and the divisions of the flows into the straightly running components and the aslant running components, mixes the blood and the diluent.

In this embodiment, blood and a diluent are introduced into the mixer 7. However, the mixer is not limited to this embodiment. For example, a gas inert to blood and diluents, such as air, may be introduced, to mix blood and a diluent and to improve the efficiency of the mixing. FIG. 8 illustrates an example of the latter embodiment. This example further has a gas channel 4E on the substrate 3 in addition to the elements of the embodiment shown in FIG. 7. The gas channel 4E, as well as the blood-transferring channel 4B, is a flexible tube. The gas channel 4E is squeezed by the rollers in the window for the rollers 3A, whereby a gas, such as air, in the channel is sent toward the mixer 7. The air is mixed with a diluent in the mixer 7 or upstream of the mixer 7, and blood is further added. In this embodiment, a gas-liquid separator 17 is disposed downstream of the mixer 7, and the liquid, which is a mixture of blood and a diluent, and a gas are separated. The separated gas together with superfluous liquid is discharged through a gas-discharging channel 4F. Sending air to the mixer 7 in this way improves the efficiency of mixing blood and a diluent. It also shortens the time period for which sampled blood is in the mixer 7 and the sample liquid-transferring channel 4D, which makes it possible to measure sampled blood quickly. The rugged part 7B corresponds to the air bubble trapping structure in the mixer 7 shown in FIGS. 15 and 16. In the embodiment shown in these figures, the introduction of air bubbles into the mixer 7 by an air bubble supplier, which is an additional member, provides the advantages explained above.

Figure 17:
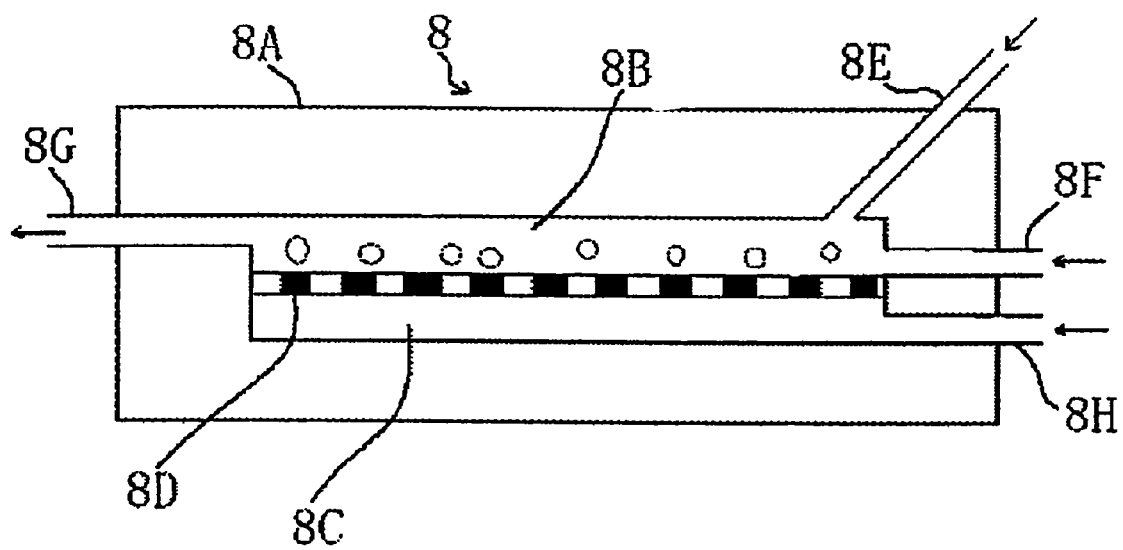
FIG. 17 is a schematic illustration showing the structure of a section of a variation of the mixer of the blood sugar level-measuring unit, which is an example of the present invention.

The mixer 7 capable of expediting the mixing of blood with a diluent by introducing air into it, as explained above, may employ, for example, the structure of a mixer 8 shown in FIG. 17. As illustrated in FIG. 17, the mixer 8 has a mixing room 8B and a gas room 8C inside the mixer proper 8A in the shape of a rectangular parallelepiped. Inside the mixing room 8B, a gas-permeable partition 8D is disposed along the flow of the liquid or a gas. The gas-permeable partition 8D divides the inside space of the mixer proper 8A into the mixing room 8B and the gas room 8C. There is no special limitation on the gas-permeable partition 8D, as long as it has a structure allowing fine gas bubbles to spout into the mixing room 8B. The gas-permeable partition may be a porous plate-like member, specific examples of which may include porous hydrophobic polymer films, porous ceramic plates, and sponges made of synthetic resins. The application of the air bubble trapping structure also to the mixer 7 shown in FIG. 17 will provide the advantages.

The mixing room 8B is provided with a diluent path 8E through which a diluent supplied through the diluent-supplying channel 6 is introduced, a body fluid path 8F through which blood transferred through the blood-transferring channel 4B is introduced, and an outlet 8G that is connected to the sample liquid-transferring channel 4D with a gas-liquid separator 17 in between. The diluent path 8E and the body fluid path 8F should be disposed at a side of the mixer proper 8A, opposite the side at which the outlet 8G is placed.

The gas room 8C is provided with a gas inlet 8H through which a gas, such as air, is introduced into and flows through the gas room 8C.

I will explain how the mixer 8 works in the followings. First, a diluent and blood are introduced into the mixing room 8B respectively through the diluent path 8E and the body fluid path 8F. On the other hand, air is introduced into the gas room 8C through the gas inlet 8H. The air having been introduced into the gas room 8C turns into fine air bubbles when the air passes through the gas-permeable partition 8D. These fine air bubbles are introduced into the mixing room 8B, and the introduced fine air bubbles stir the diluent and the blood that have also been introduced. The blood is sufficiently mixed with the diluent by the stirring, and the well-mixed fluid is drawn from the mixing room 8B through the outlet 8G.

The mixed diluent and blood is separated from fine gas bubbles by the gas-liquid separator provided downstream of the outlet 8G of the mixer 8, or next to the mixer 8.

Also, it is preferable to employ the mixer 40 in place of the mixers 7 and 8. When the mixer 40 is used in place of the mixer 7, the mixer 40 should have the blood-transferring channel 4B and the diluent-supplying channel 6, in place of the liquid inlet 42, at the location where the liquid inlet 42 has been provided, and it should have the blood-transferring channel 4B, in place of the liquid outlet 43, at the location where the liquid outlet 43 has been provided.

By neatly arranging all the members and parts that contact fluids, such as a catheter 1E, a physiological saline tank 1D, a diluent tank 1F, a calibrating liquid tank 1G, and a waste liquid tank 1H, on the substrate, an example of the medical support instrument kit according to the present invention is prepared. Biological component sensors may be those with which the medical support device proper is equipped, or those that contact fluids. By sterilizing this medical support instrument kit with a sterilizer such as ethylene oxide and packing the sterilized kit with a packing material in an isolated and sterile condition, or by packing the medical support instrument kit with a packing material in an isolated condition and sterilizing it with a sterilizer such as ethylene oxide, a package of the medical support instrument is prepared.

How an artificial endocrine pancreas device to which the blood sugar level-measuring device 2 according to the present invention has been attached works, will be explained below.
How to Measure Glucose Before beginning an operation of the artificial endocrine pancreas device, the blood sugar level-measuring unit 2 is attached to the artificial endocrine pancreas device proper 1. Specifically, the attaching pins 12 projecting from the mount table 11 are inserted into the holes for attachment 3C, and the abutment of the attaching rods to the attaching pins makes the substrate 3 firmly attached to the mount table 11. Then, the fluid channels on the substrate 3 are respectively connected to the physiological saline tank 1D, the catheter 1E, the diluent tank 1F, the calibrating liquid tank 1G, and the waste liquid tank 1H. The fluid channels are set to the roller pump, the first flow path changeover switch 1B, and the second flow path changeover switch 1C. These settings are made by connecting the respective connectors of the fluid channels with the connectors fixed to the ends of the fluid channels appended to the blood sugar level-measuring unit 2. The connection between the connectors is a very easy operation. The channel arranging and connecting operations for the artificial endocrine pancreas device are thus finished. In this embodiment, because the blood sugar level-measuring unit 2 is provided with the substrate 3 and the glucose-measuring fluid 4, it is not necessary for the operator to dispose and connect the fluid channels one by one, but just to attach the substrate 3 onto the artificial endocrine pancreas device proper 1. This unit is capable of simplifying the required operations such as disposing channels, improving workability, and decreasing the amount of work in an unhygienic condition caused by dirt of the fluid channels. Also, the fluid channels can be set to the roller pump mounted on the mount table 11 of the endocrine pancreas device, very easily by a single operation.

The catheter 1E of the artificial endocrine pancreas device is kept in the body of a patient. Then, as shown in FIG. 7, a heparin-containing physiological saline is transferred to the catheter 1E, which is a double lumen catheter, from the physiological saline tank 1D. Blood sampled through this catheter 1E is mixed with the heparin-containing physiological saline within this catheter 1E. The heparin-containing blood within the catheter is forcibly transferred through the blood-transferring channel 4B, which is squeezed by the rollers of the fluid transfer structure, to the mixer 7.

On the other hand, a diluent is transferred through the diluent-supplying channel 6 from the diluent tank 1F by the squeezing of the rollers 1A. The transferred diluent is sent to the mixer 7. In the mixer 7, as shown in FIGS. 15 and 16, the blood and the diluent are being mixed while striking against the rugged part 7B. A sample liquid is prepared by this mixing.

At this time, the first flow path changeover switch 1B blocks communication between the sample liquid-transferring channel 4D and the calibrating liquid-supplying channel 5, while connecting the blood-transferring channel 4B with the sample liquid-transferring channel 4D, which is state (1). Therefore the sample liquid flows through the sample liquid-transferring channel 4D, and enters, via the connectors 9i, the glucose sensor 4A where the glucose included in the sample liquid is measured. The data of the amount of glucose measured are transferred to a controller of the artificial endocrine pancreas device proper 1, which controller is not shown in the figures.

On the other hand, the sample liquid after the measurement is forcibly discharged to the outside of the glucose sensor 4A through the sample outlet 8j, the connectors 9i and the waste liquid-transferring channel 4C, by the squeezing of the rollers 1A. The discharged sample liquid is transferred through the waste liquid-transferring channel 4C to the waste liquid tank 1H, in which the discharged sample liquid is stored.

In this embodiment, the blood sugar level-measuring unit 2 is provided with the substrate 3 and the glucose-measuring fluid 4. In other words, each and every fluid channel is arranged on the substrate prior to the commencement of, for example, the glucose measurement operation. Therefore it is not necessary for the operator to dispose and connect the fluid channels one by one, but just to attach the substrate onto the artificial endocrine pancreas device proper. The employment of this unit makes it possible to simplify conventionally required operations such as disposing channels, and improve workability. Because the use of this unit simplifies operations such as disposing channels, it also decreases the amount of work in an unhygienic condition caused by dirt of the fluid channels. In summary, the present invention provides the blood sugar level-measuring unit 2, which is capable of improving workability, and with which the clinical examiner is able to measure blood sugar levels by hygienic operation.

After the measurement of the glucose of the patient is completed in this way, the catheter 1E that has been kept in the patient's body is taken out. The fluid channels on the substrate 3 are detached from the glucose sensor 4A, the physiological saline tank 1D, the catheter 1E, the diluent tank 1F, the calibrating liquid tank 1G, and the waste liquid tank 1G respectively, after, if necessary, the patient's blood remaining in the catheter and the fluid channels are discharged to the waste liquid tank 1H. The step of removing the substrate 3 from the artificial endocrine pancreas device proper is thus completed.

Because the substrate is provided with the fluid channels in advance, all that the operator has to do after the measurement of glucose is to detach the substrate from the artificial endocrine pancreas device proper; s/he does not have to detach the pipes of the used blood sugar level-measuring unit 2, which enables him/her to throw away the blood sugar level-measuring unit 2 without contacting fluids, such as body fluids, adhering to the elements of the units such as the pipes. Therefore also from this point of view, the present invention is capable of improving workability by providing a blood sugar level-measuring unit 2 that the operator is able to handle hygienically.

How to Wash the Glucose Sensor 4A

The blood sugar level-measuring unit 2 is attached to the artificial endocrine pancreas device proper 1 in the same way as in the measurement of glucose explained above. It is optional to keep the catheter in the patient's body.

Firstly, a diluent is transferred from the diluent tank 1 to a second diluent-supplying channel 6A via the second flow path changeover switch 1C and the first flow path changeover switch 1B, as shown in FIG. 7. The diluent is sent from the second diluent-supplying channel 6A to the calibrating liquid-supplying channel 5 by the second flow path changeover switch 1C.

Then, the first flow path changeover switch 1B chooses the flow path to the sample liquid-transferring channel 4D, whereby the diluent having flowed through the second diluent-supplying channel 6A and the calibrating liquid-transferring channel 5 is sent into the glucose sensor 4A through the sample liquid-transferring channel 4D. The inside of the glucose sensor 4A is washed with the diluent that has been transferred.

The used diluent is discharged from the glucose sensor 4A to the outside thereof by the squeezing of one of the rollers 1A that squeezes the waste liquid-transferring channel 4C through which the squeezing force is exerted on the used diluent. The discharged diluent is sent through the waste liquid-transferring channel 4C to the waste liquid tank 1H, in which the diluent is stored.

The artificial endocrine pancreas device whose glucose sensor 4 has been washed is used to measure the glucose of a patient. Alternatively, the blood sugar level-measuring unit 2 is removed from the device, and the operation of the device is stopped.

How to Calibrate the Glucose Sensor 4A

The blood sugar level-measuring unit 2 is attached to the artificial endocrine pancreas device proper 1 in the same way as in the measurement of glucose explained above. It is optional to keep the catheter in the patient's body.

Then, as shown in FIG. 7, a calibrating liquid is sent from the calibrating liquid tank 1G to the calibrating liquid-transferring channel 5 by the second flow path changeover switch 1C, and transferred through the calibrating liquid-transferring channel toward the sample liquid-transferring channel 4D.

Next, the first flow path changeover switch 1B closes the flow path that communicates with the fluid channel connected to the mixer, and makes the fluid channel from the switch 1B to the glucose sensor 4A communicate with the calibrating liquid-transferring channel 5. The calibrating liquid thus transferred from the calibrating liquid channel 5 to the sample liquid-transferring channel 4D is sent into the glucose sensor 4A. During the calibration, the glucose sensor 4 is obtaining data in the state that the calibrating liquid is being sent to the sensor. The obtained data are sent to the controller of the artificial endocrine pancreas device proper 1, which controller is not shown in the figures. Until the controller finds that the data reach a predetermined calibrated value, the calibrating liquid is continuously sent to the sensor and the sensor continues obtaining data.

After the calibration is completed, the calibrating liquid remaining in the glucose sensor 4A is discharged to the outside, by the squeezing of the rollers 1A. The discharged calibrating liquid is sent through the waste liquid-transferring channel 4C to the waste liquid tank 1H, in which the calibrating liquid is stored.

The artificial endocrine pancreas device whose glucose sensor 4 has been calibrated is used to measure the glucose of a patient. Alternatively, the blood sugar level-measuring unit 2 is removed from the device, and the operation of the device is stopped.

When a blood sugar level-measuring unit 2 is used in clinics and hospitals that have strict hygienic standards, a blood sugar level-measuring unit packed with a packing material such as a bag and sealed in an isolated condition, or a blood sugar level-measuring unit package, should be employed. The blood sugar level-measuring unit package comprises a blood sugar level-measuring unit contained in a packing material in an isolated condition. A blood sugar level-measuring unit 2 may be sterilized with, for example, ethylene oxide prior to the packing, or it may be sterilized, together with the packing material, after it is packed. The blood sugar level-measuring unit 2 may be sterilized by common sterilizing methods, such as heating or irradiation with ultraviolet rays.

The packing material may be anything as long as it is capable of containing the blood sugar level-measuring unit 2. Examples may be bags made of resins such as polyethylene or polypropylene.

Because a blood sugar level-measuring unit is kept sterile in a package of a blood sugar level-measuring unit, the clinical examiner is capable of operating an artificial endocrine pancreas device just by taking the blood sugar level-measuring unit out of the package and attaching it to the device artificial endocrine pancreas proper. Also after the operation of the artificial endocrine pancreas device, the used blood sugar level-measuring unit may be detached from the device proper and discarded. Therefore the present invention provides a safe package of a blood sugar level-measuring unit whose operability is excellent, which is hygienic, and which gives the operator fewer opportunities to contact patients' body fluids.

The blood sugar level-measuring unit in this embodiment is used to measure glucose in blood. However, it may measure body fluids other than blood from which the unit is capable of measuring glucose. Examples of such body fluids may include urine, sweat, and intercellular liquid.

In the embodiment explained hereinbefore is employed a multiple roller device as a liquid transfer means. However, a roller device having a single rotating shaft, and a single elongated roller supported by the shaft with its axis parallel to the axis of the rotating shaft may be employed. In the latter case, the roller device is so designed that fluids in all the fluid channels through which the fluids have to be transferred are transferred by the squeezing of the single roller.

Also, in the foregoing embodiment, the blood-sampling instrument, such as a catheter, is provided separately, in addition to the artificial endocrine pancreas device proper and the blood sugar level-measuring unit. However, the blood-sampling instrument may be included in, for example, the blood sugar level-measuring unit in advance.

I claim:

1. A mixing device comprising:
    a mixer including:
        an air bubble-trapping structure configured to temporarily trap air bubbles and provided to a surface of a mixing channel through which liquids to be mixed flow, wherein
        the mixing channel is provided with a liquid inlet at a part upstream of the mixing channel, from which the liquids are supplied, and a liquid outlet at a part downstream of the mixing channel, from which the liquids are discharged, and
        the liquid inlet is located at a higher level than the liquid outlet;
    either one of an air bubble supplier and an air bubble generator, positioned in the mixing channel included in the mixer to make air bubbles exist in the mixing channel; and
    a liquid supplier configured to supply liquids to be mixed either one by one or substantially simultaneously to the liquid inlet to feed the liquids into the mixing channel.

2. The mixing device according to claim 1, wherein:
    the air bubble-trapping structure is provided with a hydrophobic part formed on an inner surface of the mixing channel through which the liquids flow, and
    the mixing channel is inclined at an angle of 20 to 90 degrees to a horizontal line.

3. A medical component-measuring unit comprising the mixing device according to claim 1.

4. A mixer comprising:
    an air bubble-trapping structure configured to temporarily trap air bubbles and provided to a surface of a mixing channel through which liquids to be mixed flow
    the mixing channel is provided with a liquid inlet at a part upstream of the mixing channel, from which the liquids are supplied, and a liquid outlet at a part downstream of the mixing channel, from which the liquids are discharged, and
    the liquid inlet is located at a higher level than the liquid outlet.

5. The mixer according to claim 4, wherein the mixing channel is inclined at an angle of 20 to 90 degrees to a horizontal line.

6. The mixer according to claim 4, wherein the air bubble-trapping structure is placed in a ceiling of the mixing channel.

7. The mixer according to claim 4, wherein the air bubble-trapping structure is at least one selected from grooves, recesses and projections formed in a ceiling of the mixing channel.

8. A mixer comprising:
    an air bubble-trapping structure configured to temporarily trap air bubbles and provided to a surface of a mixing channel through which liquids to be mixed flow, wherein
    the air bubble-trapping structure is provided with a hydrophobic part formed on an inner surface of the mixing channel through which the liquids flow.

9. The mixer according to claim 8, wherein
    the mixing channel is provided with a liquid inlet at a part upstream of the mixing channel, from which the liquids are supplied, and a liquid outlet at a part downstream of the mixing channel, from which the liquids are discharged.

10. The mixer according to claim 9, wherein the liquid inlet is located at a higher level than the liquid outlet.

11. The mixer according to claim 10, wherein the air bubble-trapping structure is placed in a ceiling of the mixing channel.

12. The mixer according to claim 10, wherein the mixing channel is inclined at an angle of 20 to 90 degrees to a horizontal line.

13. A medical component-measuring unit comprising:
    a mixer including
        an air bubble-trapping structure configured to temporarily trap air bubbles and provided to a surface of a mixing channel through which liquids to be mixed flow, wherein the mixing channel is provided with a liquid inlet at a part upstream of the mixing channel, from which the liquids are supplied, and a liquid outlet at a part downstream of the mixing channel, from which the liquids are discharged, and the liquid inlet is located at a higher level than the liquid outlet.

* * * * *